US011576575B2

(12) United States Patent
Milea et al.

(10) Patent No.: US 11,576,575 B2
(45) Date of Patent: Feb. 14, 2023

(54) HAND HELD OPHTHALMIC AND NEUROLOGICAL SCREENING DEVICE

(71) Applicant: SINGAPORE HEALTH SERVICES PTE LTD, Singapore (SG)

(72) Inventors: Dan Milea, Singapore (SG); Raymond Najjar, Singapore (SG); Tin Aung, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 664 days.

(21) Appl. No.: 16/610,516

(22) PCT Filed: Apr. 27, 2018

(86) PCT No.: PCT/SG2018/050204
§ 371 (c)(1),
(2) Date: Nov. 4, 2019

(87) PCT Pub. No.: WO2018/203828
PCT Pub. Date: Nov. 8, 2018

(65) Prior Publication Data
US 2021/0393122 A1 Dec. 23, 2021

(30) Foreign Application Priority Data
May 2, 2017 (SG) .......................... 10201703570Y

(51) Int. Cl.
*A61B 3/113* (2006.01)
*A61B 5/16* (2006.01)
(Continued)

(52) U.S. Cl.
CPC ............ *A61B 3/113* (2013.01); *A61B 3/0008* (2013.01); *A61B 3/04* (2013.01); *A61B 3/102* (2013.01);
(Continued)

(58) Field of Classification Search
CPC ....... A61B 5/163; A61B 3/113; A61B 3/0008; A61B 3/04; A61B 3/102; A61B 3/112;
(Continued)

(56) References Cited

U.S. PATENT DOCUMENTS

2016/0073874 A1 3/2016 Tsai et al.
2016/0262611 A1* 9/2016 Rotenstreich ........ A61B 3/0025

FOREIGN PATENT DOCUMENTS

CN 204410781 U 6/2015
CN 105433899 A 3/2016

* cited by examiner

*Primary Examiner* — James R Greece
(74) *Attorney, Agent, or Firm* — Soroker Agmon Nordman Pte Ltd

(57) ABSTRACT

A hand-held sized ocular and neurological screening device, system and method, the screening device comprising an eyepiece and a hand-held housing, the housing comprising a tubular stimulus chamber defining a light stimulus channel, wherein an illumination source is configured to provide light stimulus towards an opening through the light stimulus channel and an operational chamber comprising an infrared camera positioned outside the stimulus channel and inclined towards the opening, the infrared camera is configured to capture images of the pupils and eye movements through the opening without interfering with the light stimulus and a controller configured to receive the captured images from the infrared camera. The hand-held sized device can include a clip-on fixture for fixing the device onto a table, a desktop, or any portable ophthalmic apparatus.

27 Claims, 22 Drawing Sheets

(51) Int. Cl.
    *A61B 3/00*         (2006.01)
    *A61B 3/04*         (2006.01)
    *A61B 3/10*         (2006.01)
    *A61B 3/11*         (2006.01)
    *A61B 3/12*         (2006.01)
    *A61B 3/135*       (2006.01)
    *A61B 3/14*         (2006.01)
    *A61B 5/00*         (2006.01)

(52) U.S. Cl.
    CPC ................ *A61B 3/112* (2013.01); *A61B 3/12* (2013.01); *A61B 3/135* (2013.01); *A61B 3/145* (2013.01); *A61B 5/0013* (2013.01); *A61B 5/163* (2017.08); *A61B 5/7264* (2013.01); *A61B 5/746* (2013.01); *A61B 5/4082* (2013.01); *A61B 5/4088* (2013.01)

(58) Field of Classification Search
    CPC ........... A61B 3/12; A61B 3/135; A61B 3/145; A61B 5/0013; A61B 5/7264; A61B 5/746
    USPC ........................................................ 600/558
    See application file for complete search history.

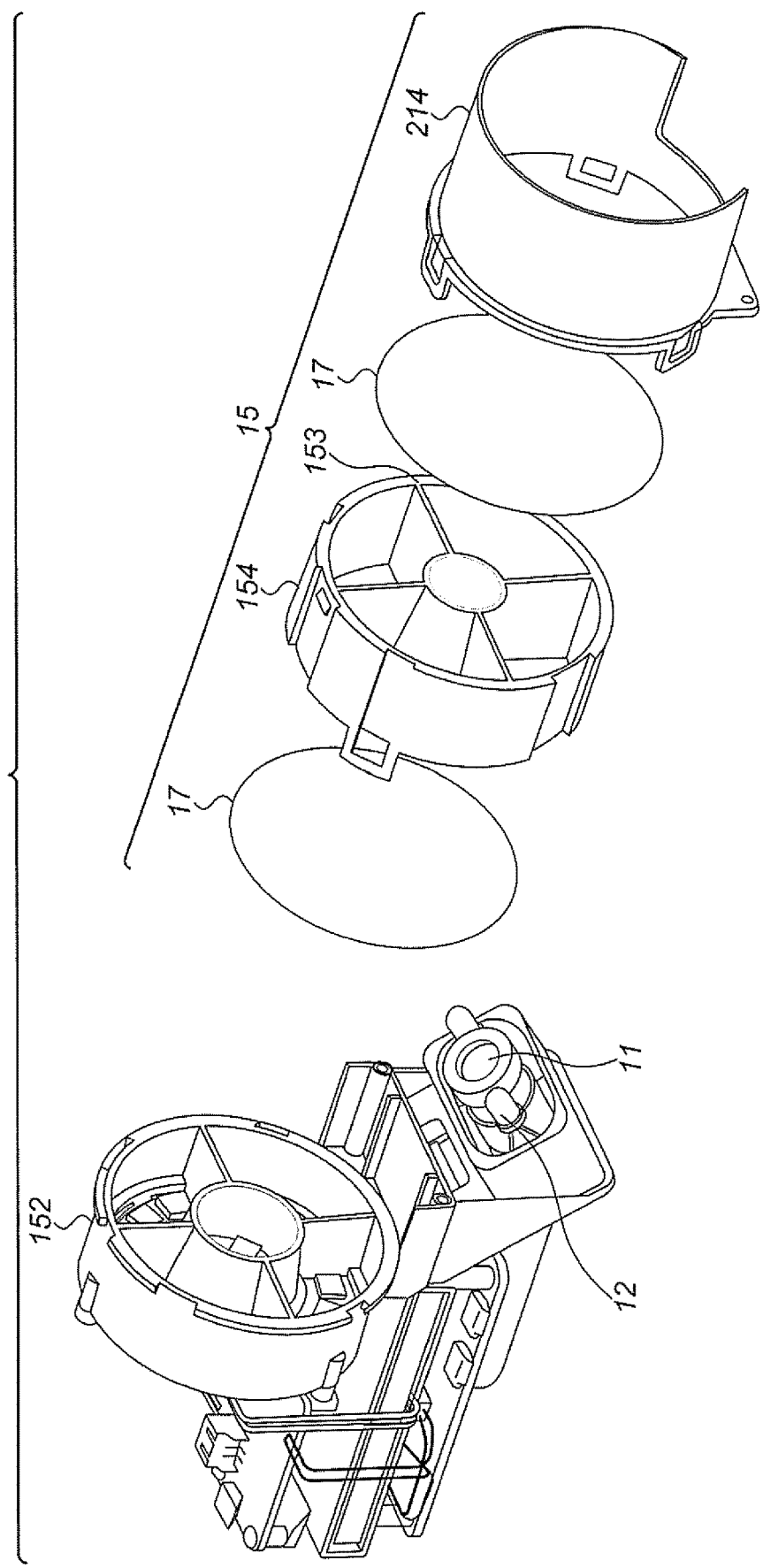

HAND HELD OPHTHALMIC AND NEUROLOGICAL SCREENING DEVICE

RELATED APPLICATIONS

This application is related to International Application serial number PCT/SG2015/050494, filed Dec. 16, 2015, published as WO2016/099402, the content of which is hereby incorporated by reference.

TECHNICAL FIELD

The present disclosure generally relates to the examination of light-induced and cognition-related pupillary responses (PLR) as well as to measurement of eye movements as an indication of ocular and neurological health, and more specifically to a handheld sized device for examining pupillary changes and eye movements.

BACKGROUND

Numerous ophthalmic conditions, such as diabetic retinopathy (DR) and glaucoma, are expected to become the most common causes of irreversible blindness worldwide, as the number of elderly patients rapidly increases. Morbidities related to these ophthalmic conditions are also on the rise, causing increased health care costs and economic burden. Such retina-affecting conditions are difficult to diagnose, especially in early asymptomatic stages, when intervention is most effective to slow the progression of the disease. At later stages, when patients experience visual symptoms, the retinal and/or optic nerve damage is most of the time irreversible and the costs of treating the disease increases significantly.

In addition to ocular pathologies, retinal dysfunction and retinal ganglion cells (RGCs) loss have been documented in several cerebral neurodegenerative diseases including dementia, Parkinson's disease, etc. Early detection of these neurodegenerative diseases and in particular in dementia (such as Alzheimer's disease, AD) is challenging but essential to slow the progression of the disease and improve patients' quality of life. Other neurological conditions, such as traumatic brain injury, are major causes of morbidity and mortality having a high societal impact. The diagnosis and prediction of such conditions is essential, yet difficult to establish at an early stage.

Abnormal pupillary responses and ocular movements have previously been observed in glaucoma and retinopathies. The methods used in these observations, however, mainly relied upon bulky lab-based equipment, usually not suitable for everyday clinical use. Other available devices require a healthcare professional to administer the test.

Current detection techniques are not ideal for effective population screening, or self-screening because they rely on time-consuming clinical examinations or image analysis, and are expensive, difficult to implement at community levels, require trained manpower, appropriate imaging techniques, and costly software. For example, screening for glaucoma requires various time consuming procedures such as Humphrey Visual Field (HVF) testing, frequency-doubling technology (FDT) perimetry, Optical Coherence Tomography (OCT) and slit lamp examination. These procedures are time consuming and expensive, and can only be implemented in dedicated clinics with trained personnel, which is a problem in deprived countries. Moreover, the HVF, predominantly used to grade the severity of visual dysfunction in ocular diseases (such as glaucoma) remains a time-consuming and subjective assessment.

Recently, more objective, yet expensive tools have evaluated the relative afferent pupillary defect (RAPD), as a proxy for retinal ganglion cell (RGC) loss. These tools, however, are limited to patients with glaucoma who exhibit asymmetric disease. Other complementary approaches are still needed to detect loss of retinal and RGC functions in patients with symmetric optic neuropathy.

SUMMARY

According to an aspect of some embodiments of the present disclosure there is provided a hand-held sized ocular and neurological screening device including: an eyepiece; and a hand-held housing including a tubular stimulus chamber defining a light stimulus channel, wherein an illumination source is configured to provide light stimulus towards an opening through the light stimulus channel; and an operational chamber including an infrared camera positioned outside the stimulus channel and inclined towards the opening, the infrared camera is configured to capture images through the opening without interfering with the light stimulus; and a controller configured to receive the captured images from the infrared camera.

Optionally, the light stimulus channel comprising an illumination panel at a distal end and an opening at a proximal end, the opening at the proximal end is configured to engage with the eyepiece.

Optionally, the controller is configured to transmit the captured images, video or any other digital signal to an external computing device associated with the screening device or directly to a cloud storage system.

Optionally, the external computing device is a user computing device.

Optionally, the external computing device is an external server.

Optionally, the controller is configured to receive instructions from an external computing device and to control the illumination panel and the infrared (IR) camera parameters according to the received instructions.

Optionally, the stimulus chamber comprises at least one optical apparatus between the illumination panel and the opening. Optionally the optical apparatus is a diffuser and/or a filter and or a lens. Optionally, the optical apparatus is located less than a distance that allows accommodation of a human eye, from a rim of the eyepiece to an eye of a user of the device.

Optionally, the operational chamber comprises at least one infrared light source outside the stimulus channel providing infrared illumination towards the opening.

Optionally, the device includes a network interface for communication with the external computing device, for example an external server. Optionally, the user computing device further communicates with the external computing device via a wide area network. Optionally, the device transfers the recorded data directly to a cloud storage system via a secured internet connection, without any interface there between. Optionally, data transfer is performed immediately after data acquisition, or post-hoc.

Optionally, the stimulus chamber comprises barriers for dividing the stimulus channel to sub channels, wherein controller is configured to control the illumination panel and the infrared camera parameters to provide illumination separately to each of the sub channels. Optionally, the barriers divide the stimulus channel to quadrant sub channels and a central sub channel.

Optionally, the eyepiece comprises an eye support having an extended lip and a connector for engagement with the opening of the housing, the connector having two opposite gaps, wherein the gaps enable the camera to capture images via the opening when the extended lip is oriented in a temporal direction.

Optionally, the infrared camera is positioned outside the stimulus channel at an inclination of about 60 degrees towards the opening through the light stimulus channel.

Optionally, the hand-held sized device further includes a clip-on fixture for fixing the device onto an apparatus selected from a group consisting of: a table, a desktop, and a portable ophthalmic apparatus. Any of the mentioned apparatuses that the hand-held sized device may be fixed onto may be located either at the user's premises or at a healthcare provider's premises. Optionally the hand-held sized device may be fixed onto any other apparatus, for example, any apparatus that may be found in a healthcare provider's office.

Optionally, the portable ophthalmic apparatus may be selected from a group consisting of: refractometers, optical coherence tomography devices, fundus cameras, slit lamp examination equipment, trial Frame Refraction, and any other device that may be present at an eye care or healthcare practitioner's office.

Optionally, the hand-held sized device includes a first arm and a second arm such that said apparatus is held between the first arm and the second arm of the device.

Optionally, the user computing device is configured to transmit an alert to the user in case calculated value implies abnormal ocular or neurological functioning.

Optionally, the user computing device employs a pre-stored examination protocol and is enabled to provide instructions to the controller based on the pre-stored examination protocol. Optionally the pre-stored examination protocol is received from the application server by means of a wide area network.

According to another aspect of some embodiments of the present disclosure there is provided a system for ocular and neurological screening including: an application server configured to communicate with a user device via a software application installed in the user device; and a hand-held sized ocular and neurological pupil screening device including an eyepiece; and a hand-held housing including a tubular stimulus chamber defining a light stimulus channel, comprising an illumination panel at a distal end and an opening at a proximal end, the opening is configured to engage with the eyepiece, wherein the illumination source is configured to provide light stimulus towards the opening through the light stimulus channel; and an operational chamber comprising an infrared camera configured to capture images through the opening without interfering with the light stimulus and to transmit the captured images, video or any other digital signal, and a controller configured to receive instructions from the application server and to control the illumination panel and the infrared (IR) camera parameters according to the received instructions, wherein the application server is configured to analyze changes in a pupil in the received images and calculate based on the changes in the pupil size or location, a value indicative about abnormal pupil or eye movement functioning.

Optionally, the application server is configured to transmit an alert to the user device in case calculated value implies abnormal ocular or neurological functioning.

Optionally, the application server is configured to receive from the user device an examination protocol and to provide instructions to the controller based on the received protocol.

Optionally, the hand-held sized pupil screening device further includes a clip-on fixture for fixing the device onto an apparatus selected from a group consisting of: a table, a desktop, and a portable ophthalmic apparatus. Any of the mentioned apparatuses that the hand-held sized pupil screening device may be fixed onto may be located either at the user's premises or at a healthcare provider's premises. Optionally the hand-held sized device may be fixed onto any other apparatus, for example, any apparatus that may be found in a healthcare provider's office.

Optionally, the portable ophthalmic apparatus may be selected from a group consisting of: refractometers, optical coherence tomography devices, fundus cameras, slit lamp examination equipment, trial Frame Refraction, and any other device that may be present at an eye care or healthcare practitioner's office.

Optionally, the hand-held sized pupil screening device includes a first arm and a second arm such that said apparatus is held between the first arm and the second arm of the device.

According to another aspect of some embodiments of the present disclosure there is provided a method for ocular and neurological screening including: providing to a controller instructions to control an illumination panel in a hand-held sized ocular and neurological screening device, the device including: an eyepiece; and a hand-held housing including a tubular stimulus chamber defining a light stimulus channel, wherein the illumination panel is configured to provide light stimulus towards an opening through the light stimulus channel; and an operational chamber comprising an infrared camera configured to capture images through the opening without interfering with the light stimulus and to transmit the captured images to an external computing device and a controller configured to receive instructions from the external computing device and to control the illumination panel according to the received instructions; receiving a stream of images from the camera; and analyzing changes in a pupil size and position in the received images and calculating based on the changes in the pupil size and position a value indicative about abnormal ocular or neurological functioning.

Optionally, the light stimulus channel comprises the illumination panel at a distal end and an opening at a proximal end, the opening is configured to engage with the eyepiece.

Optionally, the changes analyzed are in the pupil size and position over the duration of the illumination. Optionally, the changes analyzed are in the rate of change of the pupil size and position over the duration of the illumination or visual target presentation.

Optionally, the change analyzed includes at least one of a list consisting of: the amplitude of pupil constriction, latency of pupil constriction, speed of pupil constriction, baseline pupil size, pupil re-dilation speed, post-illumination pupil response, area under a pupillary response curve, the duration of the pupillary response, blink rates, fixation losses, as well as the amplitude, latency, gain, velocity and peak velocity of ocular movement, and the percent time spent in a region of interest in the presented stimulation, eye movement, eye movement amplitude, eye movement velocity, eye movement peak velocity, eye movement percent time spent in a region of interest, parameters computed via machine learning from pupillographic, and ocular movement traces.

BRIEF DESCRIPTION OF THE DRAWINGS

Some non-limiting exemplary embodiments or features of the disclosed subject matter are illustrated in the following drawings.

In the drawings:

FIGS. 3C-3E are schematic illustrations of the back-side, front-side and exploded view, respectively, of the optical module, illumination module, and circuitry of an exemplary device for ocular and/or neurological screening, according to some embodiments of the present disclosure;

FIGS. 4A-4F are schematic illustrations of various views of a device for ocular and/or neurological screening, according to some embodiments of the present disclosure;

FIGS. 7A-6E are schematic illustrations of exemplary spectral compositions of light sources and combinations thereof, according to some embodiments of the present disclosure;

Figure 1:
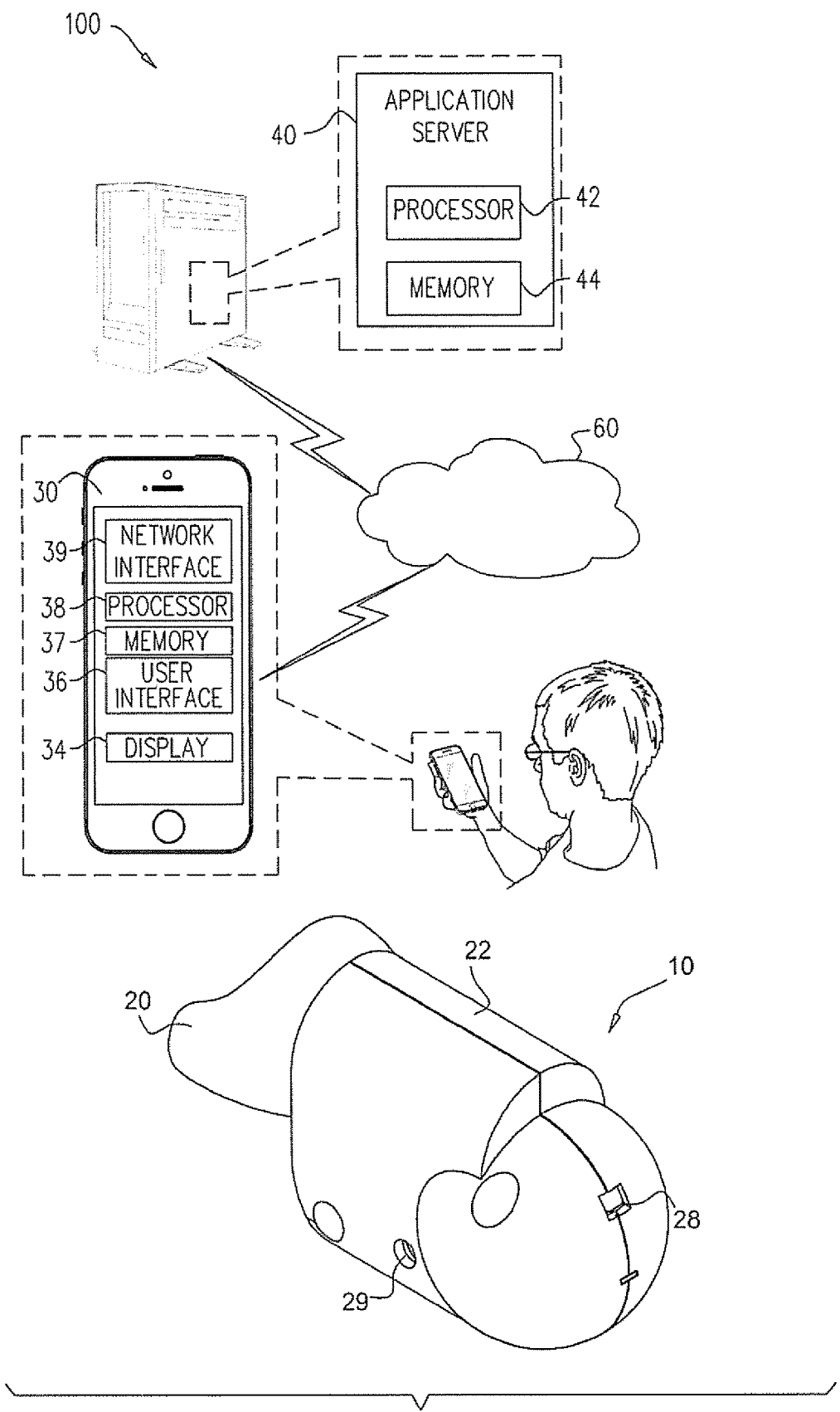
FIG. 1 is a schematic illustration of a system for ocular and/or neurological screening, according to some embodiments of the present disclosure, according to some embodiments of the present disclosure.

With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

Some embodiments of the present disclosure provide an objective, affordable and reliable ocular, neurological and eye movement-based screening tool that detects and analyses functional pupillometric and ocular movement changes in response to photic or cognitive (visual and auditory) stimulations that include but are not restricted to monochromatic, polychromatic, full field, hemi-field, quadrant, flashes, ramp-up, ramp-down, and continuous lighting regimens or a combination thereof, as well as visual and auditory cues, images, scenes, faces, videos or a combination thereof delivered by the screening device and/or the external computing device. The provided tool is hand-held sized and thus adaptable for use at a population level, which facilitates early identification of individuals with ocular and neurological dysfunctions requiring intervention and/or treatment.

The provided hand-held sized tool may be used to monitor progression of ocular diseases as well as monitor the efficacy of treatments in ocular, neurodegenerative, metabolic and systemic diseases, e.g., glaucoma, diabetic retinopathy, any optic neuropathy (compressive, inflammatory, ischemic, toxic), age-related macular degeneration (AMD), hereditary retinal and optic nerve conditions, alertness, cognitive impairment, neurodegenerative conditions (dementias, Alzheimer disease, Parkinson disease, etc.), as well as other conditions altering the vegetative system and affecting the normal functions of the pupils and/or eye movements. The provided tool may be used for self-assessment by the patient himself.

Some embodiments of the present disclosure may include a system, a method, and/or a computer program product. The computer program product may include a tangible non-transitory computer readable storage medium (or media) having computer readable program instructions thereon for causing a processor to carry out aspects of the present disclosure. Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including any object oriented programming language and/or conventional procedural programming languages.

The devices and systems of the present disclosure are capable of other embodiments or of being practiced or carried out in various ways, including as an add-on to other existing systems (i.e., in combination with other devices allowing refraction, retinal imaging, optical coherence tomography, exploration of the visual fields or of the eye movements).

Before explaining at least one embodiment of the disclosure in detail, it is to be understood that the disclosure is not necessarily limited in its application to the details of construction and the arrangement of the components and/or methods set forth in the following description and/or illustrated in the drawings and/or the Examples. The devices and systems of the present disclosure are capable of other embodiments or of being practiced or carried out in various ways.

Reference is now made to FIG. 1, which is a schematic illustration of a system 100 for ocular and/or neurological screening, according to some embodiments of the present invention. System 100 includes a device 10 for ocular and/or neurological screening, as described in detail herein. The screening device 10 may examine pupil size and pupilmetric parameters, as well as monocular eye movement. The screening device 10 may include a housing 22, an eyepiece 20, on which a user may position their eye. Optionally, screening device 10 may include an activation switch 29, a USB port 28, and/or any other suitable features as described in detail herein. In some embodiments, screening device 10 may further include a port or slot configured to accept therein a (flash) memory card, e.g., a Secure Digital (SD) card. Screening device 10 may further include a charging port to enable recharge of the power source of screening device 10.

In some embodiments, system 100 further includes a user computing device 30 and/or an application server 40. User computing device 30 may include a desktop computer, a laptop computer, a tablet computer, a computerized handheld device, a smart-phone, and/or any other suitable computing device on which a computer program may be executed to achieve the objectives of the disclosure. User computing device 30 may include at least one hardware processor 38, a network interface 39, a user interface 36, a display 34, a non-transitory memory 37, and/or any other suitable component. Application server 40 may include at least one hardware processor 42 and a non-transitory memory 44. Each of memory 37 and memory 44 may store code instructions executable by processor 38 and/or processor 42. When executed, the code instructions may cause processor 38 and/or processor 42 to carry out operations described herein.

Screening device 10 and user computing device 30 may communicate with each other, through network interface 16 (FIG. 2) and through network interface 39, respectively, such as Wi-Fi, Bluetooth, Universal Serial Bus (USB), wireless USB, cellular and/or any other suitable kind of network interfaces, for example through a wide area network 60. For example, screening device 10 is controlled by user computing device 30, for example via a dedicated software application (not shown) installed on user computing device 30. For example, a user may install the dedicated software application in computing device 30. Once the dedicated software application is installed on user computing device 30, device 30 can interact with screening device 10 and/or application server 40 via the dedicated software. The software application may include a dedicated Graphical User Interface (GUI) for interaction with a user of computing device 30. For example, processor 38 is configured to receive instructions from a user via user interface 36 and/or to display information on display 34 via the GUI. In some embodiments of the present invention, application server 40 communicates with user computing device 30 and/or with screening device 10, for example, via the software application installed on user computing device 30. For example, at least one processor 42 is configured to receive instructions from the user via user interface 36 and/or to display information on display 34 via the GUI. Processor 38 may download the software application from application server 40 and/or via an application store such as, for example, Google Play or iTunes or the like. The application server may be located in a remote location, such as for example, a secure cloud. In some embodiments, screening device 10 may transfer data (e.g., data recorded by screening device 10) directly to a cloud storage system via a secured internet connection, without any interface there between. Optionally, data transfer by screening device 10 may be performed immediately after data acquisition, or post-hoc.

In some embodiments, the software application installed on the user computing device 30 is a generic (non-dedicated) web browser or a web page interface or any computer program, which enables the download and execution of a computer program which may enable the control and/or communication between the user computing device 30 and/or the screening device 10. For example, the device 10 may be operated through a webpage/interface page executed on a web browser or other computer program and designed to control the screening device 10. The webpage/interface page may be provided by the screening device 10 or by a computer located on a network associated with the user computing device 30 once the user computing device 30 is in communication there with.

In some embodiments of the present invention, the installed dedicated software application may include one or more screening protocols for controlling screening device 10 to perform an eye screening. In some embodiments, user computing device 30, by the dedicated application, may provide the instructions to processor 42 which may control screening device 10 accordingly. For example, the screening protocols are a set of instructions according to which screening device 10 provides light stimulation to an examined eye with particular spatial and/or chronological pattern(s), intensity and/or duration, as described in more detail herein. In the present disclosure the terms screening protocols and examination protocols are used interchangeably.

In some embodiments of the present invention, once the dedicated software application is installed on user computing device 30, the dedicated GUI may prompt the user to register to the software application, e.g., to set a user account. The user also has the option to remain anonymous by skipping the registration stage. In some examples, in the latter case, user will nevertheless be provided a de-identified user number. For example, the user may be asked to enter personal details such as, for example, name, contact information, race, age, address, previous history of vision conditions, current and/or previous medical treatment, and the like. Specifically, the user may be asked to enter details about past or current vision or systemic disorders and/or neurological conditions he suffered or still suffers from, such as cataract hyperopia, myopia, presbyopia, astigmatism, glaucoma, diabetic retinopathy, vascular conditions, ocular or head trauma, neurological diseases (such cognition-impairing conditions, Parkinson's, diabetes), and the like. For example, application server 40 may receive via the GUI the information provided by the user, and may download to user computing device 30 one or more predetermined and/or preprogrammed screening protocols associated with one or more of user's personal details. In some embodiments, the application server 40 may receive instructions from a third party, for example a health professional. For example, application server 40 may download to user computing device 30 one or more screening protocols prescribed by a third party. The health professional may be located in a remote location and provide instructions and/or screening protocols and receive results of such executed protocols via currently available or later developed telemedicine of telediagnosis applications and/or systems associated with server 40 and/or directly with the screening device 10 and/or computing device 30. In some embodiments, the customization of screening protocols is also possible. Light and eye movement screening protocols may be customizable in terms of irradiance, spectral content and spatio-temporal dynamics.

In some embodiments, screening device 10 may also incorporate a Quick Response (QR) code reader or a barcode reader for patient/user identification. User identification is then transferred along with the data collected by hand-held sized screening device 10 to the secure application server or cloud.

Figure 2:
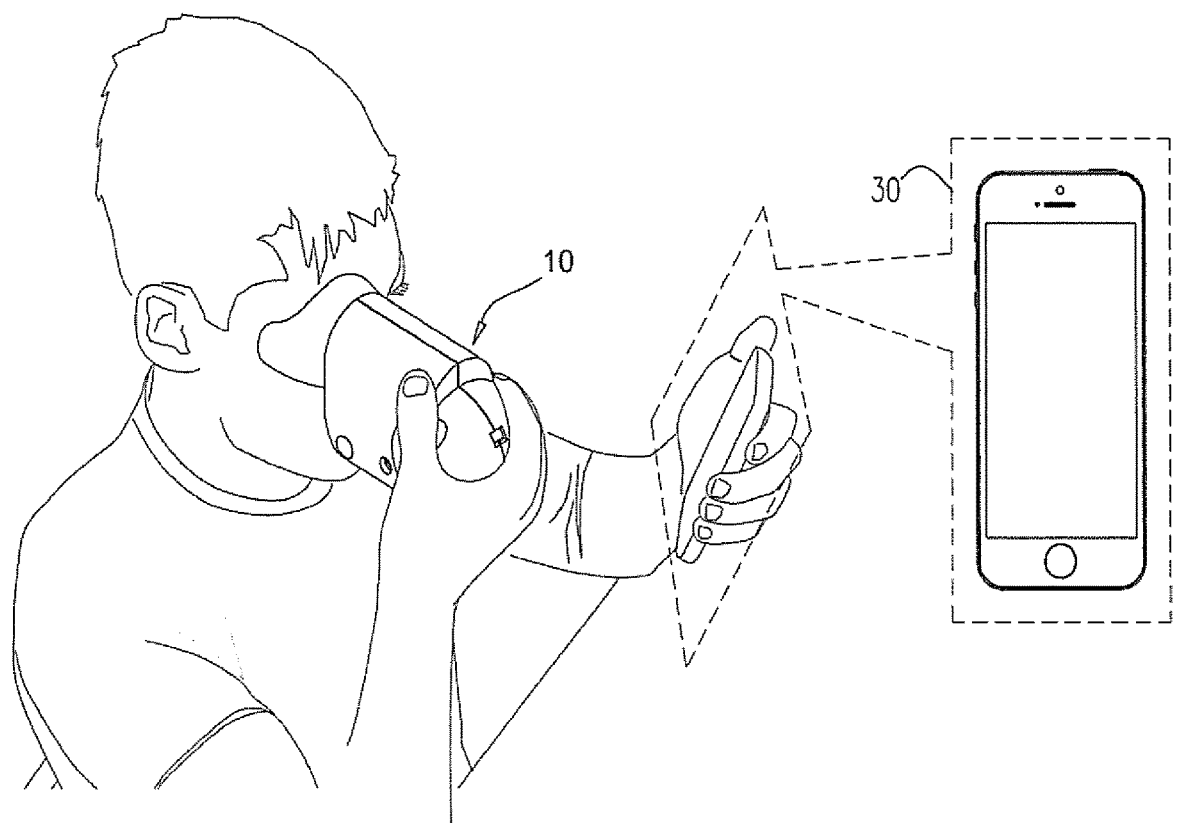
FIG. 2 is a schematic illustration of a user holding a device in one hand while the stimulus protocol is executed and watching the GUI during the execution of the stimulus protocol, according to some embodiments of the present disclosure.

Reference is now made to FIG. 2, which is a schematic illustration of a user holding screening device 10 in one hand while the screening protocol is executed, and watching the GUI during the execution of the screening protocol, according to some embodiments of the present invention. In some embodiments, the non-tested eye may be occluded to avoid artifact induced by the consensual pupillary response to light.

The user may activate the dedicated application prior to or while holding screening device 10 on the eye. User computing device 30 and/or application server 40 may receive from screening device 10 image data, video data or any other digital data depicting the user's eye, as described in more detail herein, and present the images, video or any other digital signal on display 34 via the GUI. Once ready, e.g. when the eye is properly positioned and/or the user sees and/or receives an indication via the GUI that the eye is properly positioned, user computing device 30 may receive from a command via the dedicated GUI to initiate a certain screening procedure, and/or may provide corresponding execution instructions to screening device 10. During execution of the screening procedure, user computing device 30 and/or application server 40 may receive from screening device 10 image data depicting the user's eye, as described in more detail herein, analyze the image data in real-time, and/or display on display 34 the image data along with visual indications about the examined eye and/or the screening results. Therefore, in some cases the user may monitor during the execution of the procedure the behavior of their eye in real-time to ensure proper positioning of the screening device 10. It is noted that prior to commencement of the procedure and depending on the type of procedure being administered, the screening device 10 or the computing device 30 may provide a visual or audible indication to the user to close the eye that is not subject to the procedure. For some procedures, the non-examined eye is kept open, for example, when visual cues are provided to the user being tested via the computing device, for example, when pictures are shown to the user being tested to stimulate cognitive responses. In some embodiments, the computing device 30 may be clipped orthogonally to the eyepiece 20 of the screening device 10, or to a suitable location on said device 10, to ensure the user is reading or watching the visual cues. Once the procedure is completed, user computing device 30 may present on display 34 the screening result, for example along with a recommendation for further actions. For example, in case the screening results imply a high risk of ocular or neurological malfunction, user computing device 30 may present an indication that the user should be examined by a professional. A list of nearby professionals may be provided.

In some embodiments of the present invention, a user may self-administer a screening device 10 test with the screening device 10. In some embodiments of the present invention, the user may hold screening device 10 against their eye and initiate an examination protocol, for example by the GUI displayed on user computing device 30. The user may hold screening device 10 in one hand while the stimulus protocol is executed by screening device 10 and watch the GUI in user computing device 30 during the execution of the stimulus protocol, as shown in FIG. 2. In case user computing device 30 is a mobile and/or hand held device, the user may hold computing device 30 in their free hand while holding screening device 10 in the other hand. In other cases, a user may watch the GUI in a desktop display while holding screening device 10 against their eye and/or during execution of the stimulus protocol. In operation, the user to whom the test is administered is cued when to close the non-examined eye by the computing device 30. Thus, the changes in the pupil parameters and/or the eye movement parameters may be seen and analyzed in real time during the examination on computing device 30. The ocular tests may also be administered by any healthcare provider (e.g. ophthalmologist, neurologist, general practitioner, nurse) or non-healthcare provider personnel (e.g. pharmacist, medical equipment vendor, optometrist, optician, etc.).

Figure 3A:
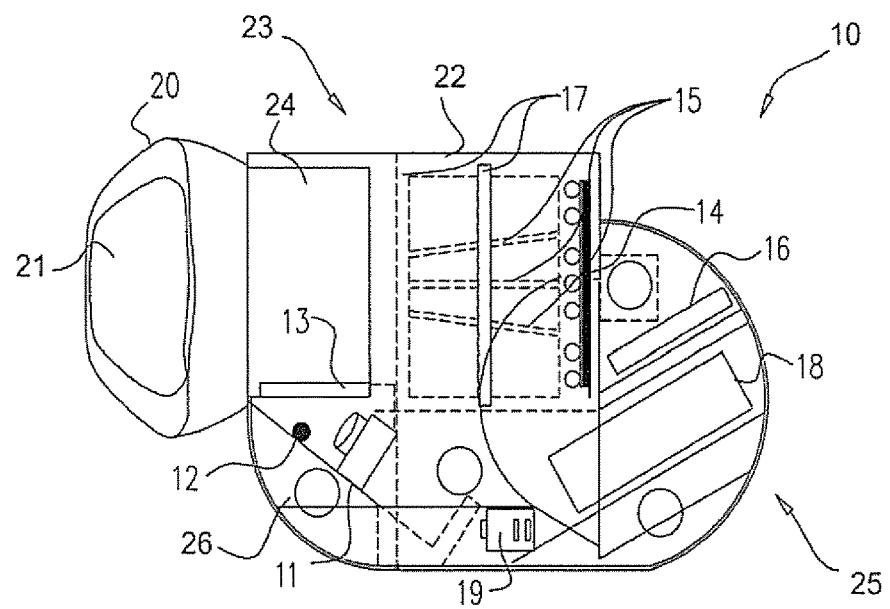
FIG. 3A is a schematic cross section illustration of an exemplary a device for ocular and/or neurological screening, according to some embodiments of the present disclosure.

Further reference is made to FIG. 3A, which is a schematic illustration of screening device 10 for ocular and/or neurological screening, according to some embodiments of the present invention. According to some embodiments of the present invention, screening device 10 is a portable hand-held device configured to perform screening for ocular or neurological pathologies.

Screening device 10 may include a housing 22 and an eyepiece 20. Housing 22 may be shaped to enable a comfortable grip by the user, such that the user may use the screening device 10 using a single hand and/or without the assistance of a healthcare professional. In some embodiments, housing 22 includes a tubular optical stimulus chamber 23 and an operational chamber 25. For example, optical stimulus chamber 23 encompasses an optical stimulus assembly including, for example, an illumination panel 14, a quadrant sectioning assembly 15, diffuser/filter/lens holders 17 and a void chamber 24. For example, optical stimulus chamber 23 has a back wall at a distal end, at which illumination panel 14 may be installed, and an open proximal end of void chamber 24, on which eyepiece 20 may be installed. The optical stimulus assembly may define an optical stimulus channel configured to provide stimulating illumination to a user's eye, as described in more detail herein. For example, illumination panel 14 may include a Red, Green and Blue (RGB) Light Emitting Diode (LED) or any other suitable combination of monochromatic or polychromatic illumination source, as described in more detail herein, for example with reference to FIG. 6. The dimensions of screening device 10 may be designated for safe use, high-quality screening and comfortable hand-holding by the user, for example, healthcare provider and/or patient. Exemplary dimensions of screening device 10 are described in more detail herein below with reference to FIGS. 4A-E.

Operational chamber 25 encompasses an operational assembly configured to operate screening device 10 to capture, detect and/or output data about reactions of a user's eye to the stimulus. The operational assembly may include an Infrared (IR) camera 11, an IR light source 12, an IR filter 13, a network interface 16, a microcontroller which may be equipped with a wireless transmission module 18 and a power source 19. IR camera 11 may be positioned at an angle, such that a line of sight of camera 11 may go through IR filter 13 and void chamber 24. IR light source 12 may be positioned on either side of the IR camera 11 or around its aperture. Void chamber 24 and other areas of the interior of tubular optical stimulus chamber 23 are preferably painted with a high reflectance white paint. Such paint enables a lesser light attenuation and a broader retinal surface light coverage. IR filter 13 may be located over IR camera 11 and/or IR light source 12, e.g. between void chamber 24 and IR camera 11 and/or IR light source 12, thus, for example, improving image quality by suppressing non-IR light interference. An exemplary camera 11 may include, for example, at least 5-megapixel resolution, maximal optical size of about 0.25 inch, f/1.8 aperture, about 3.6 mm adjustable focal length, about 75.7 degrees view angle and/or about 2592×1944 pixels still picture resolution. An exemplary camera 11 may support 1080p (30 fps), 720p (60 fps) and VGA 640×480p (90 fps) videos. The position of IR camera 11 at an angle which may be in some embodiments at an incline of about 60 degrees relative to the user's/patient's eye when the eye is facing the distal end of screening device 10. In some embodiments, the position of IR camera 11 at a bottom inclination relative to the eye of the user is preferable as the upper eyelid of the user's eye tends to be at a lower position when the user's eye faces forward. Such IR camera 11 position is more likely to receive images of the pupil without the interference of the upper eyelid.

The tubular optical chamber 23 may include a second illumination panel of dim RGB LEDs (not shown) that allow for the generation of focalized fixation points and focalized fixation cues so as to guide various types of eye movements (saccades, pursuit and the like). The second illumination panel may be located at the proximal side facing the eyepiece 20 opening 216 of FIG. 4E or in other location such that the user of the screening device 10 may visual cues enabling the fixation of the eye to illuminated LED.

Power source 19 may include a replaceable and/or rechargeable battery, and/or a port for power input from an external power source (not shown). For example, power source 19 may include a lithium battery, for example a 4.5 volt rechargeable battery, and/or may power microprocessor 18, camera 11, IR light source 12, panel 14 and/or any other suitable component. Housing 22 may include an on/off switch 29 (FIG. 1), for example to connect and/or disconnect power supply to elements of screening device 10. The on/off switch can also be equipped with an RGB LED that will indicate the status of the battery and other aspects of the device (connected, not connected, ON, OFF, Battery low, etc.). Microcontroller 18 may control, for example, illumination panel 14 and/or illumination units included in panel 14. In some embodiments, microcontroller or board computer 18 may include a Raspberry PI Zero or Raspberry PI Zero-W controller or the like, and/or may be operable by Python script or any other suitable type of instructions. Housing 22 may include a recharging module and/or a USB port 28 for recharging power source 19. In some embodiments, housing 22 may further include a port or slot configured to accept therein a memory card, e.g., a Secure Digital (SD) card. In some embodiments, microcontroller 18 includes at least one of a 1 Ghz central processing unit (CPU), a single-core CPU, a 512 MB random access memory (RAM), a mini High-Definition Multimedia Interface (HDMI) port, a universal series bus (USB) On-The-Go port, a Micro USB power port, a hardware attached on top (HAT)-compatible 40-pin header, a composite video header and/or a reset header, and an integrated Wi-Fi module.

Figure 3B:
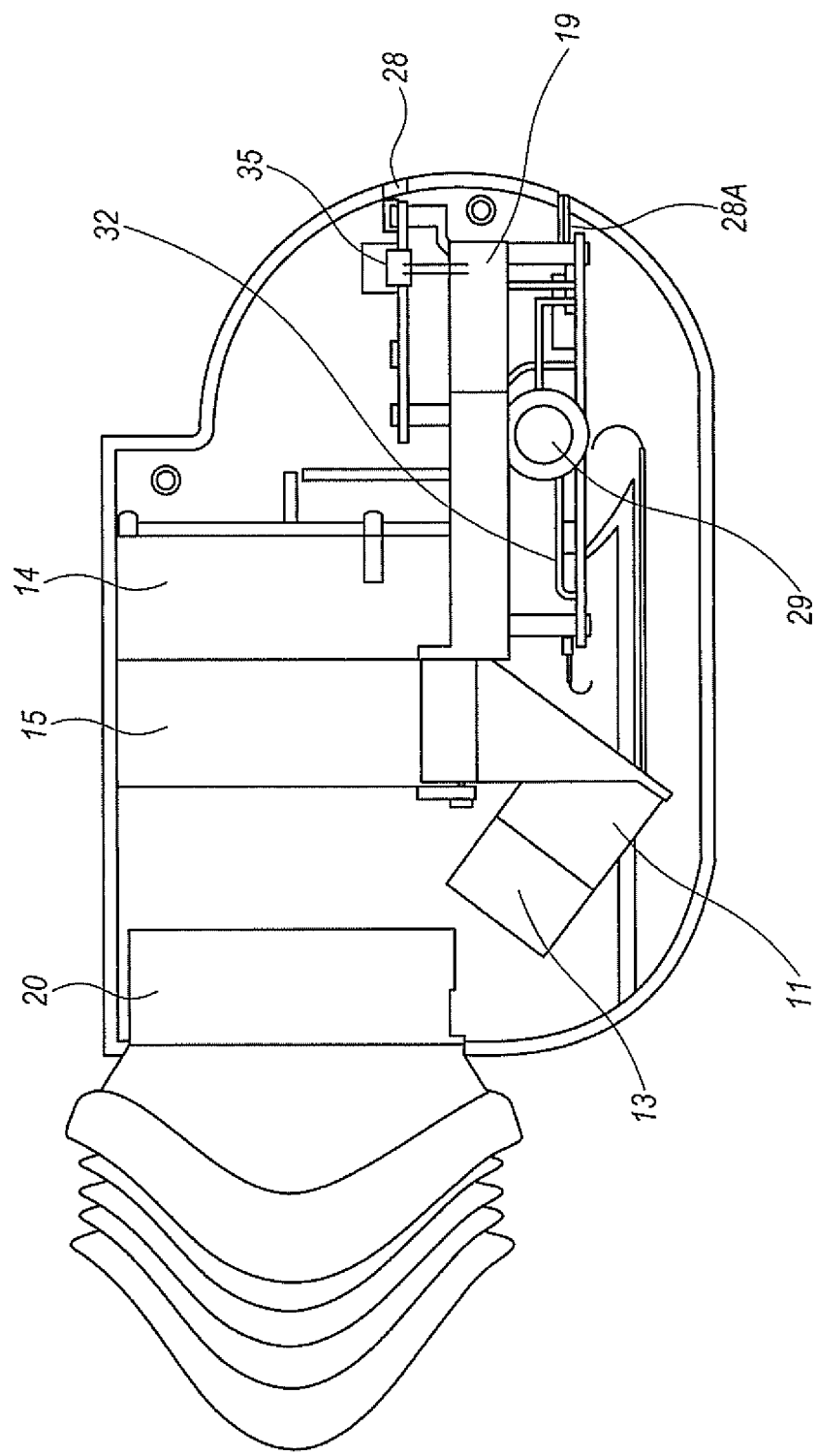
FIG. 3B is a schematic side-view of an exemplary device for ocular and/or neurological screening, without half of the housing such to enable view of inner components, according to some embodiments of the present disclosure.

Reference is now made to FIG. 3B, which is a schematic side-view of an exemplary device for ocular and/or neurological screening, without half of the housing such to enable view of inner components, according to some embodiments of the present invention. FIG. 3B illustrates the relative locations of the components of screening device 10. As mentioned with respect to FIG. 3A, screening device 10 may include eyepiece 20, which may be rotatable. Screening device 10 may further include housing 22, which may house the internal components, e.g., illumination panel 14, optics module 15, which may include lenses, diffusers and filters, as detailed throughout the disclosure. Screening device 10 may further include charging module 35, which is configured to enable charge or recharge of power source 19 via charging port 28. Screening device 10 may further include a port or slot 28A for the insertion or placement of a memory card, e.g., SD memory card. Screening device 10 may include an activation port 29, which may include an on/off button for activating or deactivating screening device 10. Screening device 10 may include a camera 11 configured to capture images of the user's eye. In some embodiments camera 11 may include an IR filter 13 for filtering out non-IR light and thus enable capturing IR images of the user's eye without non-IR light interference. Screening device 10 may include a circuit board 32, to which all electrical components (e.g., camera 11, activation switch 29, SD card slot 28A, power source 19, illumination panel 14, charging module 35 and charging port 28) are connected through wires. In some embodiments, circuit board 32 may be a printed circuit board (PCB).

Figure 3D:
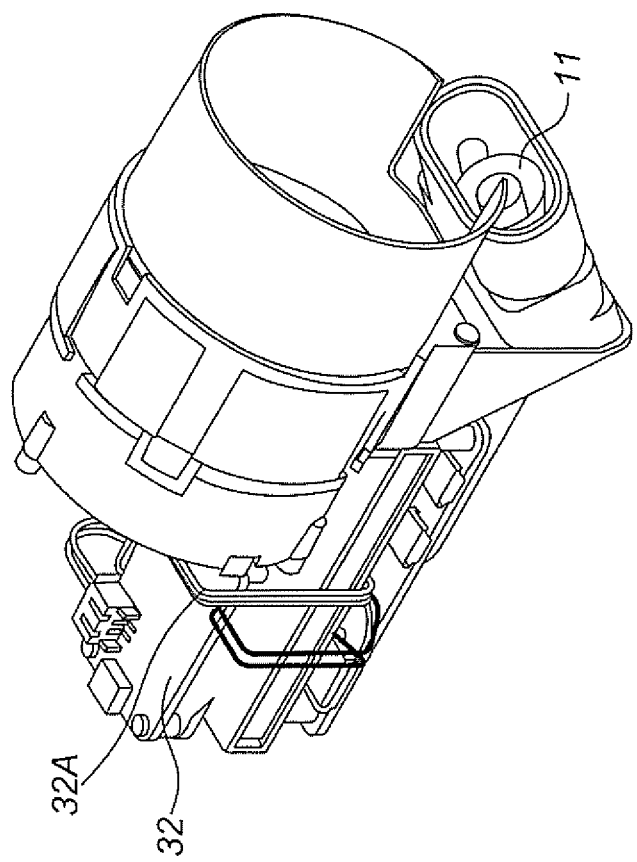
Figure 3C:
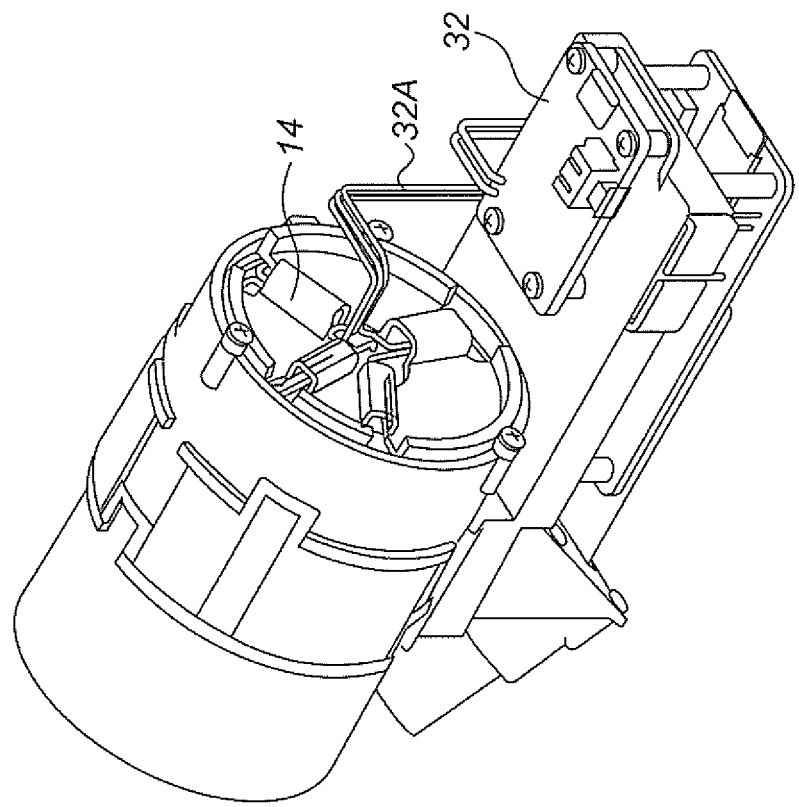

Reference is now made to FIGS. 3C-3E, which are schematic illustrations of the back-side, front-side and exploded view, respectively, of the optical module, illumination module, and circuitry of an exemplary device for ocular and/or neurological screening, according to some embodiments of the present invention. As illustrated in FIG. 3C, illumination module or illumination panel 14 may by connected to circuit board 32 via circuitry 32A. The front-side of the inner components of screening device 10 is illustrated by FIG. 3D, where camera 11, which may include IR filter 13, may be positioned. FIG. 3E, illustrates an exploded view of the optical module 15. Optical module 15 includes holders 17, which are an optical apparatus such as for example, one or more filter(s) and/or diffuser(s) and/or lens(s), located between connector 214 (FIG. 4D) configured to physically connect eyepiece 20 to housing 22 and conical tube barrier 152 (FIG. 4D). In some embodiments, one of holders 17 is further located adjacent to radial barrier wings 153 and 154 (FIG. 4D), as detailed herein. The exploded view of FIG. 3E illustrates IR illumination source 12 and it position with respect to camera 11. In some embodiments, IR illumination source 12 may include more than one illumination source. Typically, one or more IR illumination sources 12 are located at the periphery of camera 11.

Figure 3F:
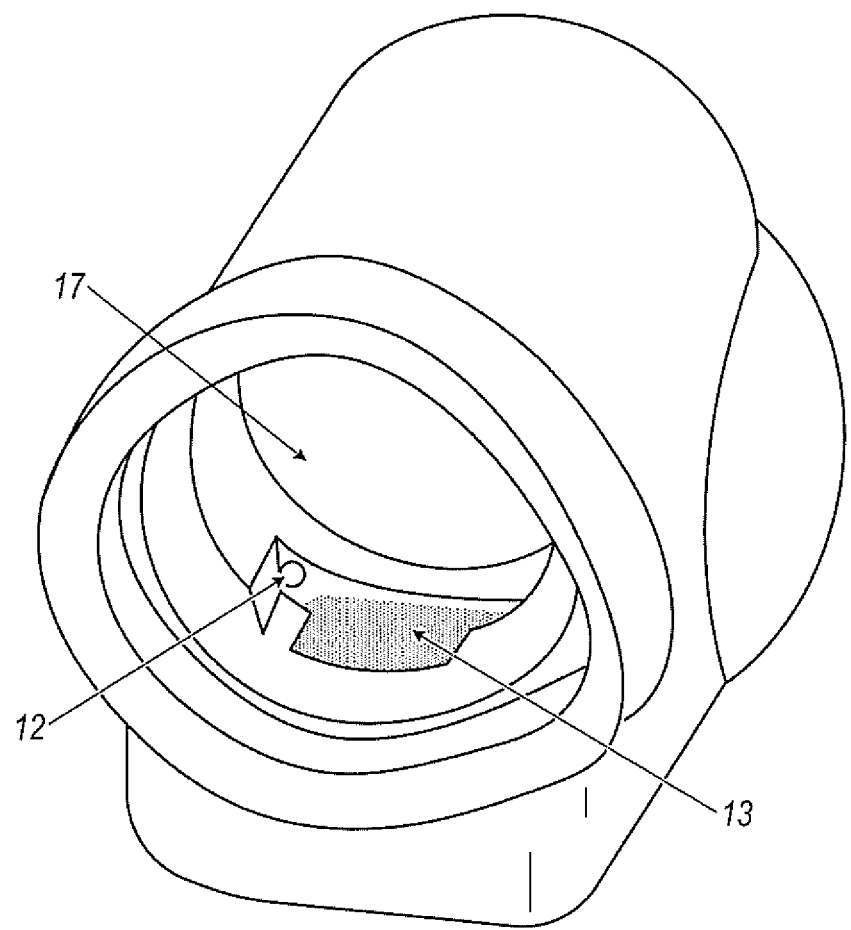
FIG. 3F is a schematic illustration of a perspective view of an exemplary device for ocular and/or neurological screening, according to some embodiments of the present disclosure.

Reference is now made to FIG. 3F, which is a schematic illustration of a perspective view of an exemplary device for ocular and/or neurological screening, according to some embodiments of the present invention. FIG. 3F illustrates eyepiece 20 through which a few components may be noticeable, e.g., IR filter 13, which may be located over camera 11 (not shown), IR illumination source 12 located at the side or periphery of IR filter 13 (and of camera 11), and one of the optical elements of holders 17, e.g., a diffuser, a filter or a lens.

Figure 4A:
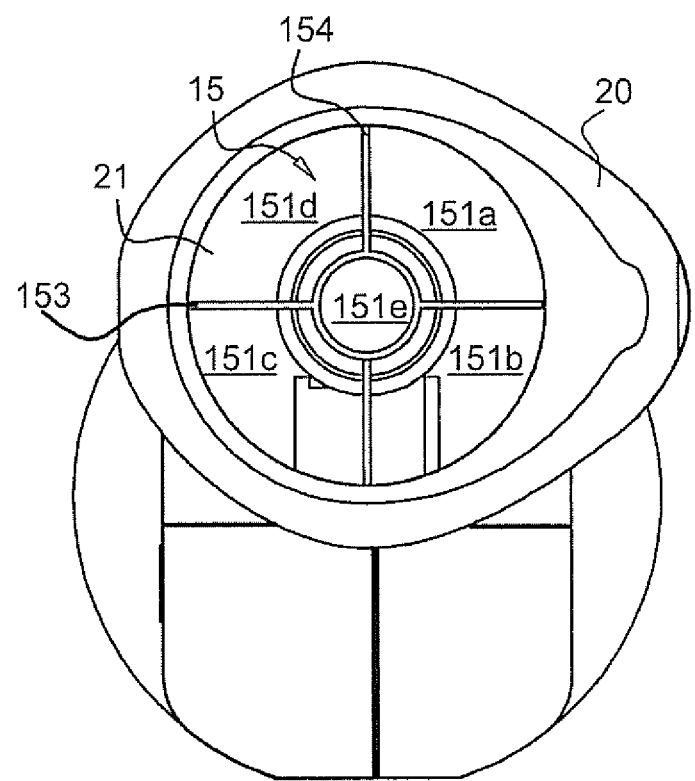
Figure 4B:
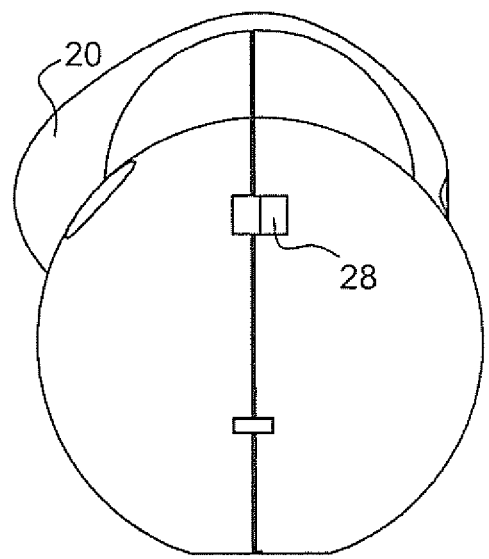
Figure 4C:
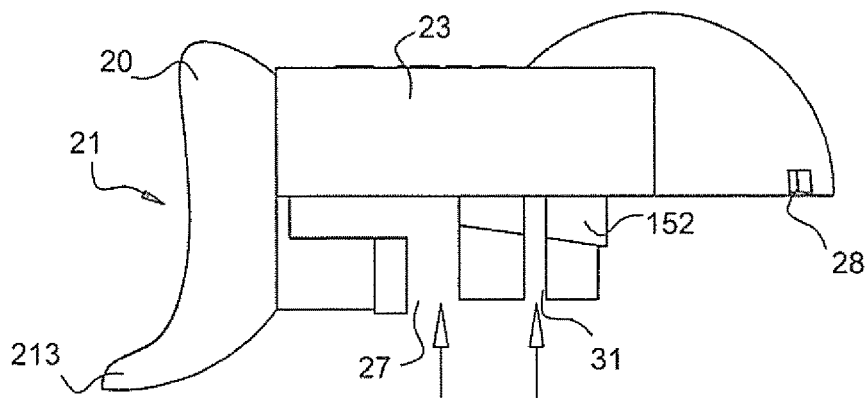
Figure 4D:
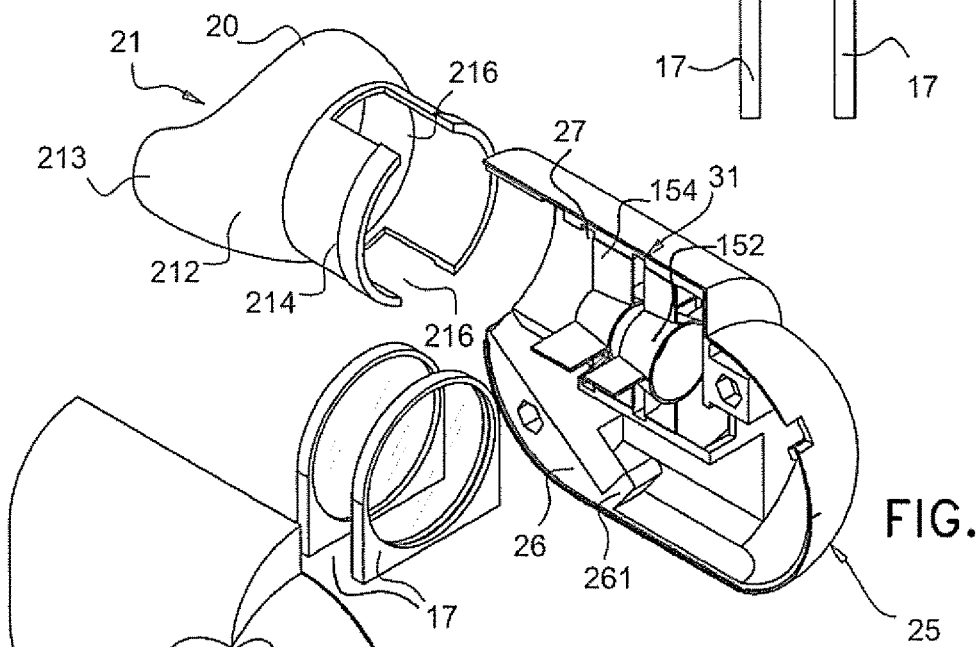

Further reference is made to FIGS. 4A-4E, which are schematic illustrations of various views of screening device 10 for ocular and/or neurological screening, according to some embodiments of the present invention. FIG. 4A shows quadrant sectioning assembly 15, which may divide the optical stimulus channel to sub-channels.

Sectioning assembly 15 may include, for example, radial barrier wings 153 and 154 that enable projection of light to a specific portion of the eye's retina, for example according to a predetermined pattern. Sectioning assembly 15 may channel light separately, for example, via respective sub-channels 151a-151d, to the superior temporal, inferior temporal, inferior nasal and superior nasal portion(s) of the eye, for example while sparing the macula, or including illumination to the macula via sub-channel 151e. Sectioning barrier assembly 15 may include a conical tube barrier 152 (Shown in FIGS. 4C and 4D) that defines internal sub-channel 151e. A diameter of conical tube barrier 152 may decrease towards void chamber 24, e.g. may be maximal at a distal end facing panel 14 and minimal at a proximal end facing void chamber 24. Sectioning barrier assembly 15 may include wing barriers such as barriers 153 and 154 extending radially from conical barrier 152, which divide the optical stimulus channel to peripheral sub-channels. For example, barrier assembly 15 may include horizontal wing barriers 153 that divide the optical stimulus channel to superior and inferior portions and vertical wing barriers 154 that divide the optical stimulus channel to temporal and nasal portions. FIG. 4B shows a behind/back view of screening device 10, showing the round shape of screening device 10 and port 28.

Figure 4E:
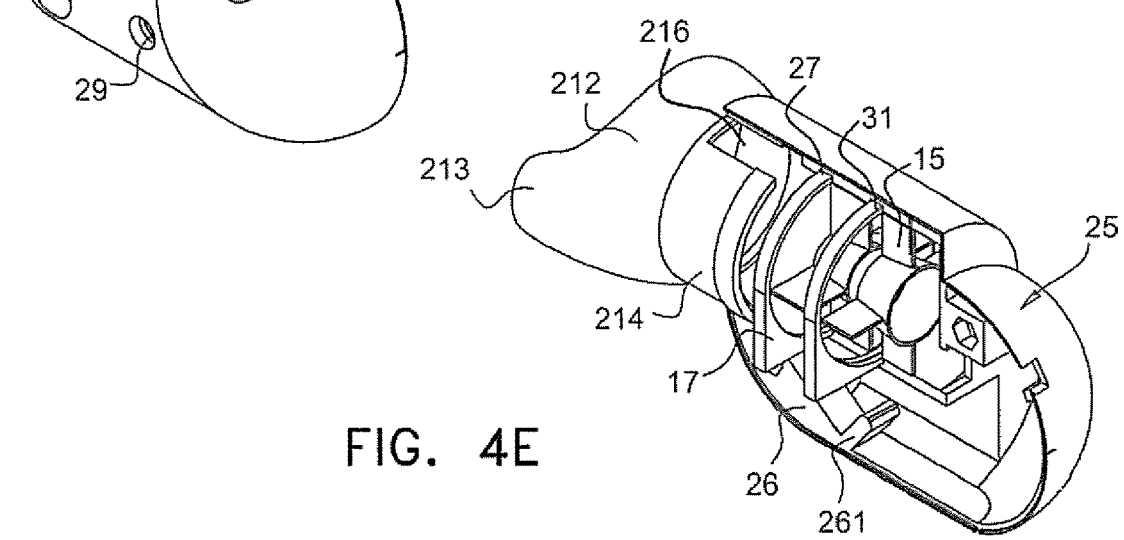

In some embodiments of the present invention, as shown in FIGS. 4C-4E, optical stimulus chamber 23 may include at least one slot 27, but preferably two slots, 27, and 31 located before, after and/or across assembly 15. A width of one or more slots 27, and 31 may match a width of holder 17, to enable insertion, removal and/or replacement of holder 17 in one or more slots 27, and 31. In some embodiments holders 17 are an optical apparatus such as for example, one or more filter(s) and/or diffuser(s) and/or lens(s). The one or more optical apparatus(es) are preferably located in one or more slots 27, and 31. Holders 17 may hold or serve as the filter and/or the diffuser and/or the lens, through which the illumination from panel 14 may pass, to filter and/or diffuse the illumination as required. Holders 17 and/or the optical apparatus (such as filter(s) and/or diffuser(s) and/or lens(s)) may be replaced according to specific requirements of a screening protocol or required examination and/or use intended for the device.

During operation of system 100, a user may hold screening device 10 against their eye, e.g., place the cup of eyepiece 20 on their eye, and illumination panel 14 may provide light through the optical stimulus channel, e.g., through assembly 15, at least one filter and/or diffuser and/or lens, and void chamber 24, towards an opening 21 of eyepiece 20, for example, in a predetermined pattern and/or various optional patterns. One or more diffuser(s) may be held by a holder 17 and may be placed in one or more slots 27, and 31 in front of assembly 15, in order to diffuse light exiting assembly 15.

As further shown in FIGS. 4C and 4E, eyepiece 20, which is preferably light tight, may include an eye support 212, on which a user's eye area may be placed with the eye positioned against opening 21, and a connector 214 configured to physically connect eyepiece 20 to housing 22. IR light source 12 may provide IR illumination towards opening 21 via an opening 216 in connector 214 and void chamber 24, for example through IR filter 13. Eye support 212 may include elastomer such as rubber or silicone or any other suitable elastic material for comfortable and/or light-isolating positioning of a user's eye. Eye support 212 may be configured to provide light isolation, for example so that light provided to a user's eye via opening 21 is not interfered by external light. For example, eye support 212 is asymmetrically cup-shaped, such that its shape conforms to the eye area and/or isolates the eye area from external light, when placed over the eye area. For example, eye support 212 includes a lip 213 that extends at one side of support 212, making the cup-shape of eye support 212 asymmetrical. In some embodiments, eye support 212 may have an opaque color such that external light cannot enter through it and thus not interfere with light provided to the user's eye.

As further shown in FIGS. 4D and 4E, in some embodiments of the present invention, eyepiece 20 is removable from housing 22, for example for replacement and/or cleansing. The dimensions of eyepiece 20 may be designed and/or vary so as to enable accommodation to the size and/or shape of the user's eye area, and/or to provide a safe distance between a user's eye and the illumination panel 14. For example, eyepiece 20 may be provided in various dimensions and may be replaced as required.

In some embodiments, eyepiece 20 is rotatable in housing 22 to a desired orientation for adaptation to a user's eye area shape, which may change between users, and/or when replacing between left and right eyes of the same user. Such rotation of the eyepiece 20 to, for example, prefixed sites (not shown) also enables the placement of the eyepiece 20 such that minimal amount of external light enters the operational chamber 25 during the operation of screening device 10. It is desirable to restrict to minimum the amount of external light entering operational chamber 25 so as to enable consistent light levels exposures during the conduct of the test applied by screening device 10 to the same or various users. For example, connector 214 may include at least one opening 216 and one or more arc-shaped protrusions that match an opening of chamber 23, for example to enable rotatable connection by close-fit insertion of the protrusion(s) into chamber 23. For example, connector 214 includes two opposite arc-shaped protrusions separated by opposite openings 216. One of the arc-shaped protrusions is on the same side of eyepiece 20 as extending lip 213, and the direction of opposite openings 216 is vertical to the direction in which extending lip 213 is located. Therefore, for example, when support 212 is in a desired orientation, e.g., when extending lip 213 is oriented in a temporal direction, one of openings 216 is located in a vertical direction, so as to enable capturing of images by camera 11 via an opening 216. In some embodiments, when support 212 is in a desired orientation, openings 216 are located at the directions of vertical wings 154 and lip 213 is oriented in the direction of horizontal wings 153.

Accordingly, as mentioned above, IR camera 11 may be positioned at an angle, such that a line of sight of camera 11 may go through IR filter 13, opening 216 in eyepiece 20 and void chamber 24. When a user's eye is positioned on eyepiece 20, IR camera 11 may capture images of the eye illuminated by IR light source 12. For example, IR Light source 12 may include an IR Light Emitting Diode (LED). For example, IR camera 11 is oriented and focused to capture clear images of the eye and pupil. For example, operational chamber 25 includes an inclined platform 26 having a surface inclined in a suitable angle, upon which camera 11 may be installed to capture images from an angle, from below the optical stimulus channel and/or without interfering with and/or blocking the optical stimulus provided by illumination panel 14. For example, the inclination angle of the camera, relative to the direction of the stimulus channel, may be between about 30 and 75 degrees, or between about 40 and 75 degrees, depending upon the exact dimension of various portions of screening device 10.

The location of camera 11 along platform 26 may be adjusted, for example, for focus adaptations. Platform 26 may include a protrusion 261 to limit the movement of camera 11 along platform 26 and/or to provide a maximal and/or minimal focal distance of camera 11. For example, camera 11 may capture a stream of images of an eye while stimulus is applied to the eye, and transmit the stream of images, video or any other digital signal to processor 42, which may analyze the stream of images and detect the pupil, as described in more detail herein.

Figure 5:
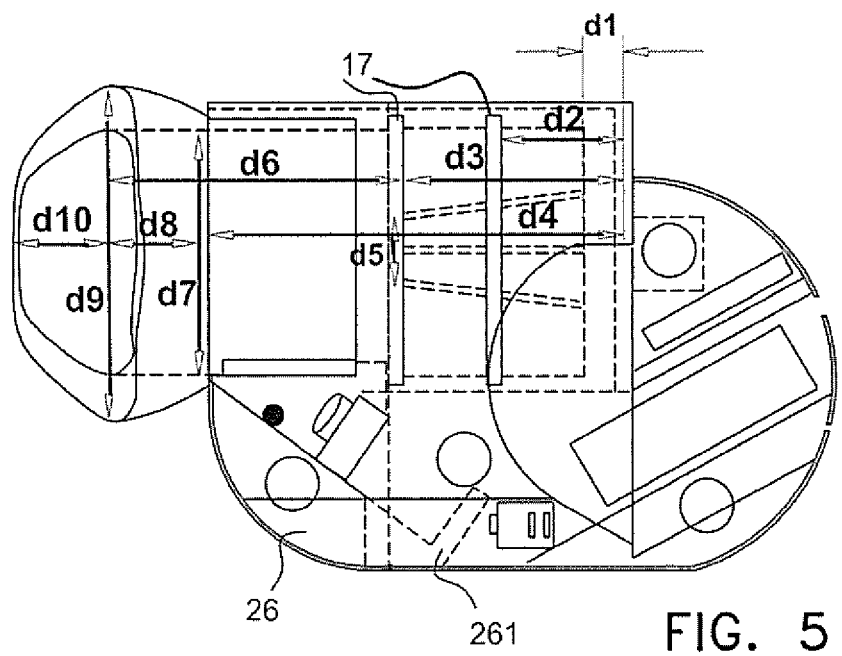
FIG. 5 is a schematic illustration of a device for ocular and/or neurological screening, according to some embodiments of the present disclosure.

Reference is now made to FIG. 5, which is a schematic illustration of screening device 10 for ocular and/or neurological screening, according to some embodiments of the present invention. The dimensions of screening device 10 may be designated for safe use, high-quality screening and comfortable hand-holding. For example, screening device 10 may weigh less than 600 grams, for example 575 grams. For example, the dimensions of screening device 10 may be configured to enable comfortable gripping of the device by hand. In some embodiments, a height and/or width of screening device 10 may be less than 10 centimeters, for example 9.6 centimeters or 8 centimeters. The length of screening device 10 may be within a range of 12-20 centimeters, but other variations may occur, depending on the precise scope. In some embodiments, the length of screening device 10 may be about 17 centimeters. Housing 20 may have round shape posterior handgrip allowing comfortable handling.

In some exemplary embodiments, a distance d1 between panel 14 and assembly 15 may be of about 4-5 millimeters, for example 4.5 millimeters. In some exemplary embodiments, a distance d2 between panel 14 and a filter, held by a first holder 17 across assembly 15, may be of about 25 millimeters, for example 24.5 millimeters. In some exemplary embodiments, a distance d3 between panel 14 and a diffuser, held by a second holder 17 in front of assembly 15, may be of about 45 millimeters, for example 44.5 millimeters. In some exemplary embodiments, a distance d4 between panel 14 at a distal end of chamber 23 and a proximal end of chamber 23 may be of about 85 millimeters, for example 84.5 millimeters. In some exemplary embodiments, an internal minimal diameter d5 of conical barrier 152 may be of about 12-16 millimeter, for example 14 millimeter. In some exemplary embodiments, an average distance d6 between a diffuser in front of assembly 15 to a rim of eye support 212, for example where the cornea is placed during operation, may be of about 55-65 millimeters, for example 60 millimeters. In some exemplary embodiments, the internal diameter d7 of opening 21 and/or of connector 214 of eyepiece 20 may be of about 45-55 millimeters, for example 50 millimeters. In some exemplary embodiments, an average distance d8 between the proximal end of chamber 23 and a rim of eye support 212, for example where the cornea is placed during operation, may be of about 18-22 millimeters, for example 20 millimeters. In some exemplary embodiments, an external diameter d9 of eye support 212 may be of about 66-70 millimeters, for example 68 millimeters. In some exemplary embodiments, a distance d10 between a rim of eye support 212, for example where the cornea is placed during operation, and an edge of extending lip 213 may be of about 18-22 millimeters, for example 19.8 millimeters.

The distances of various elements of device 10 from the cornea during operation, such as distances d6, d8 and/or d10, may depend on the bone structure of the user. For example, at distance d6 of about 55 to 65 millimeters, a full field discoid light of about 50 millimeters may directly stimulate 42 to 49 degrees of the visual field, and indirectly, for example through light reflected by high reflectance paint coating the inside of the device, may stimulate 120 to 150 degrees. Usually, a distance d6 of less than 65 millimeters between the diffuser and the user's eye prevents accommodation to the fixation zone, thus enabling monitoring of the neutral pupil response to the stimulation, e.g. unaffected or minimally affected by accommodation.

Figure 6:
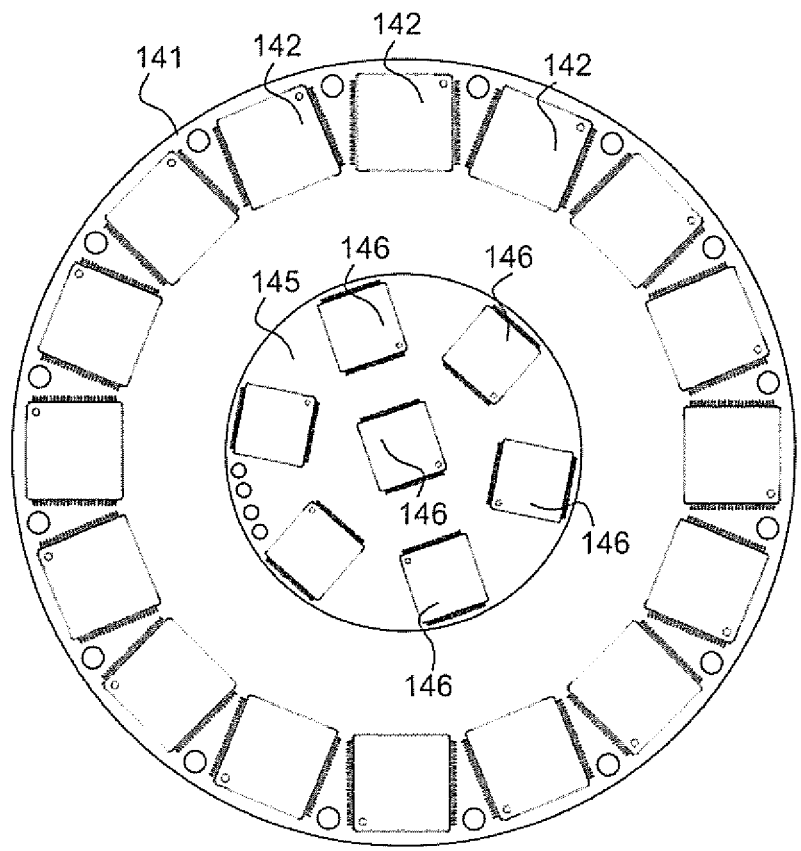
FIG. 6 is a schematic top-view illustration of an exemplary illumination panel, according to some embodiments of the present disclosure.

Reference is now made to FIG. 6, which is a schematic top-view illustration of an exemplary illumination panel 14. For example, illumination panel 14 may include an outer illumination ring 141 and an inner illumination cluster 145. In some embodiments, illumination ring 141 may have an outer diameter of about 50 millimeters, and inner illumination cluster may have an outer diameter of about 15 millimeters. For example, illumination ring 141 may provide illumination to peripheral stimulus sub-channels 151a-151d (FIG. 4A) and/or for stimulation of peripheral portions of an eye. For example, illumination cluster 145 may provide illumination to a central stimulus sub-channel 151e (FIG. 4A) and/or for macular stimulation.

Illumination ring 141 may include a plurality of illumination sources 142 such as, for example, RGB LEDs, arranged in a circle. In some embodiments of the present invention, each illumination source 142 and/or a group of illumination sources 142 is controllable separately by microcontroller 18, for example, based on instructions received from processor 42. For example, illumination ring 141 may include multiple groups of illumination sources 142, for example, four groups, corresponding to respective sub-channels separated by barrier cluster 15. Each group may include the illumination sources 142 that project light into the respective sub-channel.

Inner illumination cluster 145 may include a plurality of illumination sources 146 such as, for example, RGB LEDs. For example, cluster 145 may include multiple sources 146 arranged in a circle, for example with a light source 146 in the middle of the circle. In some embodiments, each of sources 146 is controllable separately and/or sources 146 are controllable as a group by microcontroller 18, for example based on instructions received from processor 42. For example, illumination sources 146 may project light towards opening 21, for example via central sub-channel 151e.

Figure 7A:
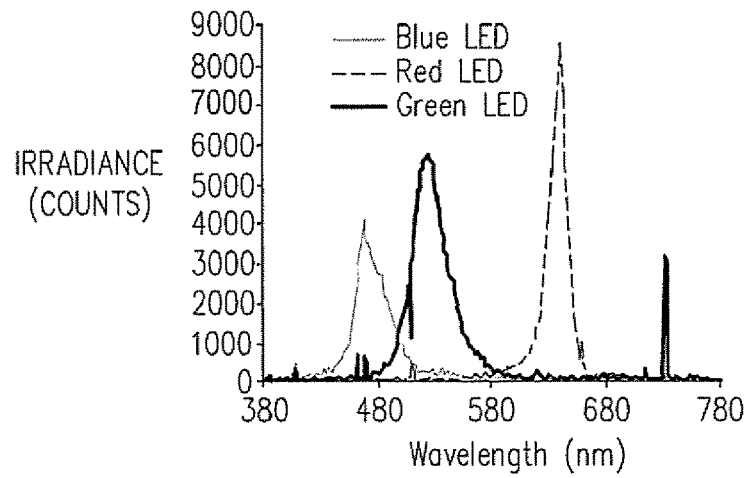
Figure 7B:
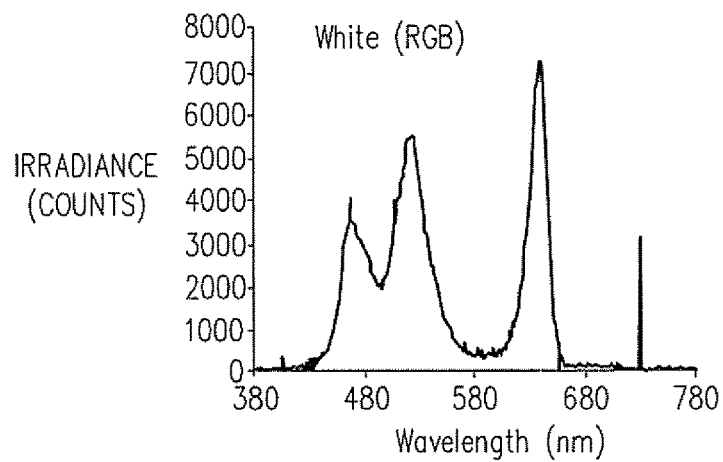
Figure 7C:
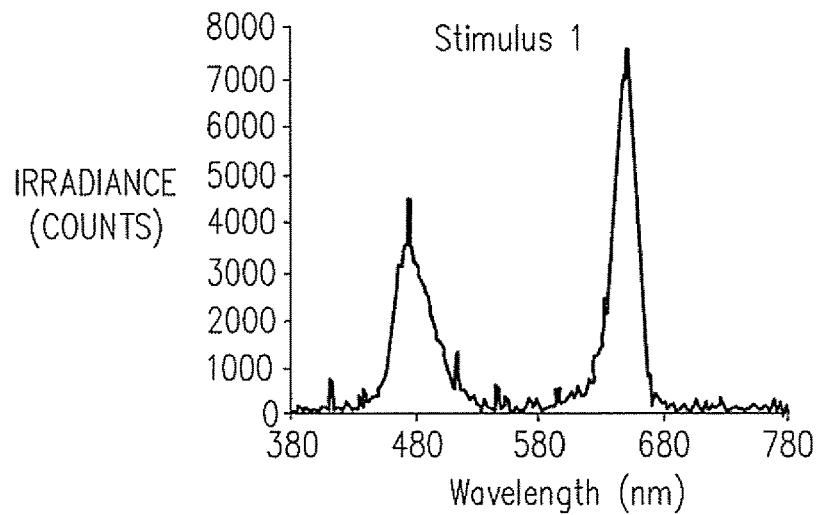
Figure 7D:
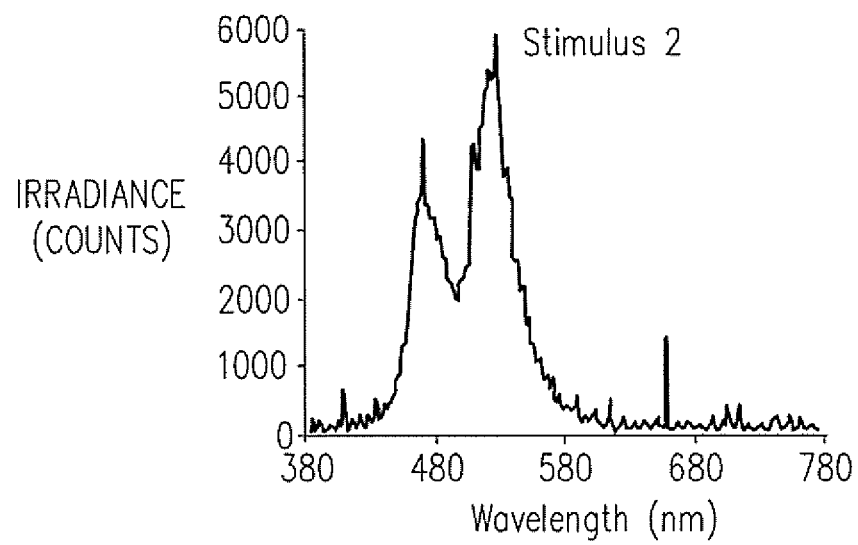
Figure 7E:
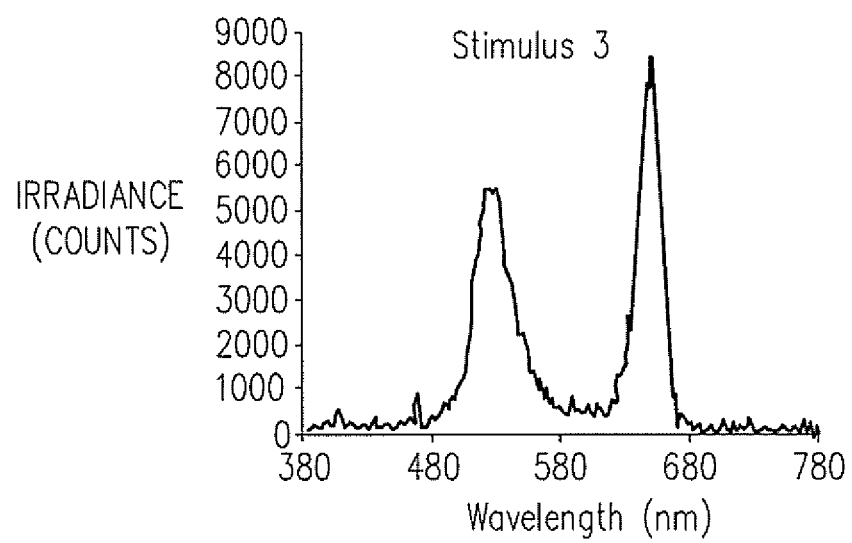

A chromatic configuration of illumination sources 146 may be contingent upon respective intensities of multiple monochromatic LEDs, wherein each source 146 may include multiple monochromatic LEDs such as monochromatic red, green and blue LEDs, exemplary spectral compositions of which is shown in FIG. 7A. Exemplary technical features of monochromatic LEDs that may be included in illumination sources 146 are detailed in the following table:

| Color | Wavelength (nanometers) [range] | range of full width at half maximum (nanometer) | Luminous intensity (millicandelas) |
|---|---|---|---|
| Red | 640 [600-680] | 10-40 | 550-700 |
| Green | 523 [500-555] | 10-40 | 1100-1400 |
| Blue | 469 [460-490] | 10-40 | 200-400 |

The resulting chromatic configuration may include a polychromatic combination such as white, yellow, purple, pink, etc., exemplary spectral compositions of which are shown in FIGS. 7B-7E.

The intensity of the monochromatic LEDs may be controlled, for example, by microcontroller 18, for example based on instructions from processor 42. The intensity of each LED 142 and/or 146 may be controlled to vary between 0 Log photons/cm2/sec and 15.5 Log photons/cm2/sec. For example, a user may control the intensity, spectral composition and/or pattern of illumination sources 146 by a GUI of a software application stored on computing device 30, via processor 42 of application server 40. For example, in order to provide sufficient stimulus to the eye, the intensity of each illumination source 146 may be controlled to vary, continuously, sequentially or in any combination of the above, possibly adapted to the pupillary's size, between 6 Log photons/cm2/sec and 15.5 Log photons/cm2/sec. In some embodiments, additional channels and illumination sources may be integrated into illumination panel 14 to allow for specific polychromatic stimulations allowing isolation of photoreceptors using silent substitution approach.

Figure 8:
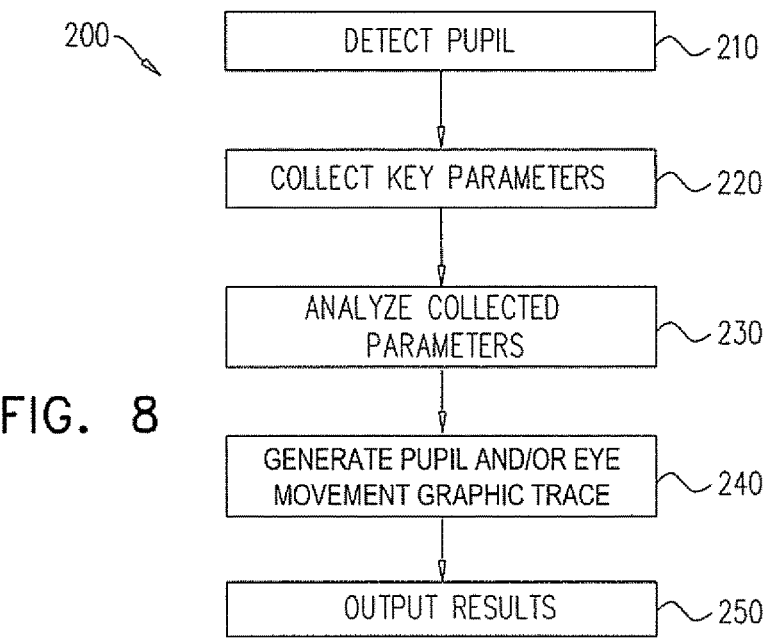
FIG. 8 is a schematic flowchart illustrating an ocular and/or neurological screening method, according to some embodiments of the present disclosure.

Further reference is now made to FIG. 8, which is a schematic flowchart illustrating an ocular and/or neurological screening method 200, according to some embodiments of the present invention. Memory 44 of application server 40 and/or memory 37 of computing device 30 may store code instructions executable by processor 42 and/or processor 38. When executed, the code instructions may cause processor 42 and/or processor 38 to carry out operations of method 200 described herein.

As indicated in block 210, processor 42 and/or processor 38 may detect the pupil in image data received from IR camera 11. As described herein, IR camera 11 may capture a stream of images of an eye while stimulus is applied to the eye, and transmit the stream of images, videos or any other digital signal or data to processor 42 and/or processor 38, which may analyze the stream of images, videos or digital data and detect the pupil.

As indicated in block 220, processor 42 and/or processor 38 may collect key parameters of the pupil, for example based on size and/or shape changes of the pupil during the screening procedure, or changes in the movement of the eye, as described in detail herein. Changes in pupil size and/or eye position are collected in response to one of the following: direct photic stimulations delivered by the illumination stimulus; cognitive and attention engaging visual cues using of illumination stimulus (such as illumination panel 14 of FIG. 3) or the display 34 via user interface 36 on the computing device 30 (of FIG. 1), for example, smooth pursuit of a sequence of chromatic light quadrants, equiluminous light illusions, facial expressions, scenes, and the like; cognitive and attention engaging auditory paradigms using a speaker (not shown) which may be located on the screening device 10 or on the computing device 3, for example, oddball task, and the like. A real-time monitoring of eye movement and pupil size during the provisions of such cues will allow for the detection of early signs of impairments in the afferent and efferent light detection and transmission pathways; impairments in the cognitive top-down control of pupil size; impairments in the cortical and sub-cortical control of eye movement.

As indicated in block 230, processor 42 and/or processor 38 may analyze the collected parameters, in order to determine risk for ocular and/or neurological abnormalities, which may require examination by a health professional. As indicated in block 240, processor 42 and/or processor 38 may generate a pupil-graphic trace for display via the dedicated GUI. The pupil-graphic trace may be a pupil size graphic trace or an eye movement graphic trace, or a graph including at least one of a list of parameters consisting of the amplitude of pupil constriction, latency of pupil constriction, speed of pupil constriction, baseline pupil size, pupil re-dilation speed, post-illumination pupil response, area under a pupillary response curve, and eye movement amplitude, velocity, peak velocity, percent time spent in a region of interest, or other parameters computed via machine learning from pupillographic and ocular movement traces. As indicated in block 250, processor 42 and/or processor 38 may output results of the screening, which may include recommendation for action to be performed by the user and/or other output, as described in detail herein.

Figure 9A:
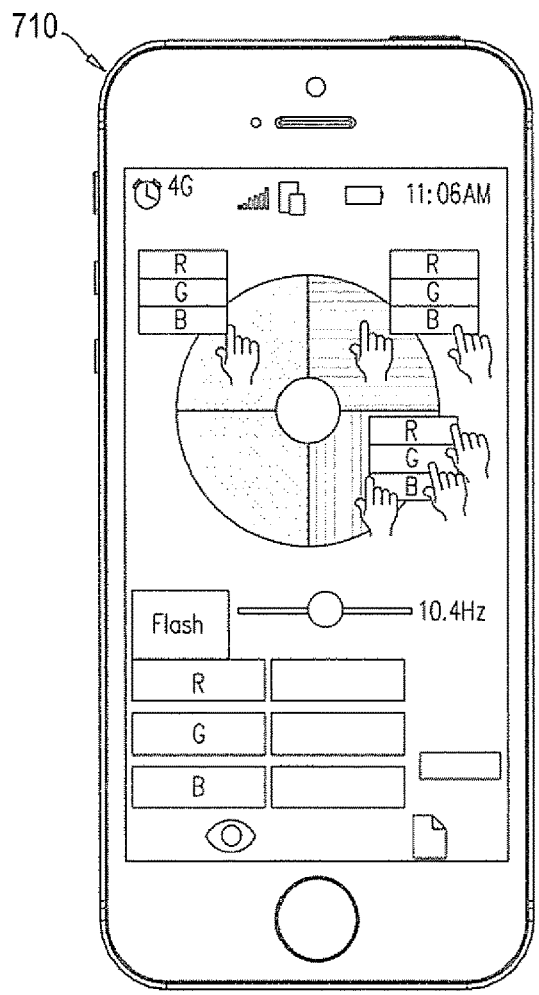
FIGS. 9A and 9B are schematic illustrations of GUI screens, according to some embodiments of the present disclosure.
Figure 9B:
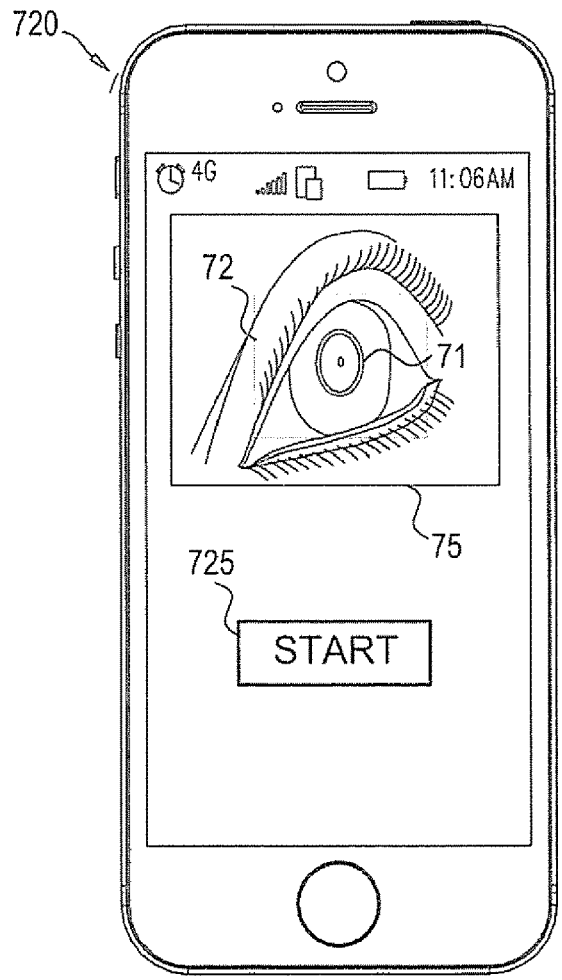

Reference is now made to FIGS. 9A and 9B, which are schematic illustrations of GUI screens 710 and 720, which may be displayed on a display 34 of computing device 30, according to some embodiments of the present invention. For example, by GUI screen 710, the user and/or a health professional may control configurations of illumination stimulus provided by panel 14, by selecting the desired configurations on GUI 710, thus providing corresponding instructions to processor 42 and/or processor 38. Processor 42 and/or processor 38 may pass commands to microcontroller 18, which may control illumination sources 146 to provide light according to the required stimulus configuration.

For example, by GUI screen 710, a user may control, e.g. by providing instructions to processor 42 and/or processor 38, spatial pattern illumination by sources 142 and/or 146, e.g. which of channels 151a-151e operate. For example, a user may control whether the illumination distribution is quadrant (for example via one of channels 151a-151d), peripheral circular or semi-circular (for example via all or some of channels 151a-151d), full field (for example via all channels 151a-151e), central discoidal (for example via channel 151e), and/or any other suitable spatial configuration of the illumination. For example, by GUI screen 710, a user may control chromatic configuration of illumination sources 146, e.g., may select a color of stimulus illumination in each of the operating channels 151a-151e. Processor 42 may pass commands to microcontroller 18, which may control illumination sources 146 to provide light according to the required illumination distribution, for example by operating only the illumination sources 146 facing the required channels.

For example, by GUI screen 710, a user may control illumination duration, chronological pattern, intensity (from 8.5 log photons/cm$^2$/s to 15.5 log photons/cm$^2$/s) and/or flashing frequency (0.1 Hz to 18 Hz) of illumination sources 142 and/or 146, separately, in groups or together. As described in more detail herein, application server 40 may receive, execute and/or store a predefined stimulus protocol, including a certain illumination pattern or a series of patterns, for example designated for screening of a specific disease, disorder or condition. By GUI screen 710, a user may select a predefined stimulus protocol to be executed by device 10.

The predefined stimulus protocol may include, for example, a gradual lighting intensity ramp-up regimen validated as effective for testing glaucoma, for example a ramp-up from about 8.5 log photons/cm$^2$/s to 14.5 log photons/cm$^2$/s. The predefined stimulus protocol may include, for example, a regimen of ramp-up and then ramp-down, or vice versa. The predefined stimulus protocol may include, for example, single or a sequence of monochromatic and/or polychromatic light flashes, for example each of about 1 ms to 1 s with a defined intensity calibrated to be safe for the user. The predefined stimulus protocol may include, for example, constant intensity light exposure, with a defined intensity calibrated to be safe for the user. The predefined stimulus protocol may include, for example, predefined and/or user controlled spatial illumination distribution, e.g. full field, peripheral field, quadrant field or macular field, e.g. central field. Other stimulus protocols may include, for example, a gradual lighting intensity ramp-down, illumination flashes and/or a darkness period and/or a gradual shift of illumination between quadrants and colors or both. In some embodiments, for example, after selecting a predefined protocol, the user may customize configuration of the illumination protocol, for example by customizing the spectral, spatial and temporal patterns of the illumination distribution, flash frequency, and/or any other suitable customization.

Figure 10A:
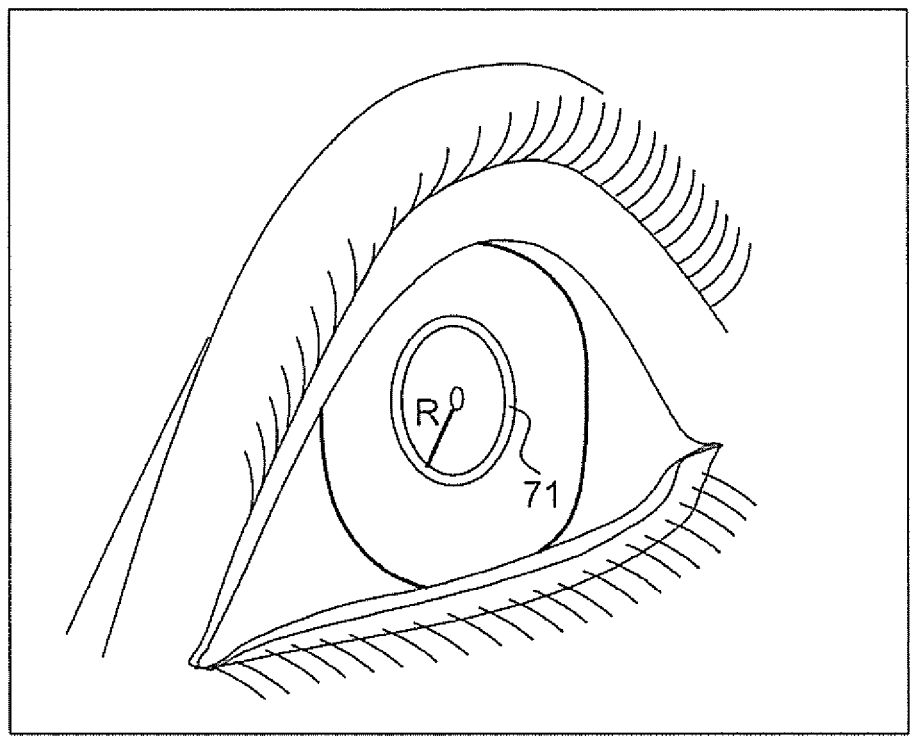
FIG. 10A is a schematic illustration of a display of images along with corresponding overlay pupil contour and/or size value and a pupil-graphic trace, according to some embodiments of the present disclosure.

By GUI screen 720, processor 42 and/or processor 38 may present to a user processed images captured by camera 11 of the user's eye during stimulus applied by device 10, for example with overlay generated by processor 42, to show the eye's response to the stimulus. For example, screen 720 may include a current captured image 75 of the eye (also shown in FIG. 10A), along with current pupil contour overlay 71 calculated by processor 42, showing the current detected pupil contour. Captured image 75 may be an image captured in real time by IR camera 11. IR Camera 11 may capture and transmit in real time images, videos or any other digital signals of the user's eye to computing device 30. For example, processor 42 and/or processor 38 may detect the contour of the pupil in the images and/or calculate the detected pupil's size and display image 75 on screen 720, together with calculated overlays such as the pupil contour and/or size value and/or position. Screen 720 may include additional overlays over image 75, such as, for example, an indication of a current calculated pupil size, for example a horizontal and vertical radius or diameter value or area of the pupil, for example in pixels and/or millimeters, and/or a frame 72 that marks the detection area or region of interest on the image, e.g. the area on the image in which parameters are detected by processor 42 and/or processor 38. In some embodiments, detection area frame 72 is displayed in a certain color during examination, e.g. while the stimulus protocol is executed, and/or may change its color when the examination is over.

In some embodiments, once the pupil is detected accurately on display 34, an audible or visual indication may be provided to the user or healthcare professional that they may push a start button 725 or activation switch 29 (FIG. 1), which may initiate an examination procedure. In some embodiments, once a user or a healthcare provider sees that the eye is positioned properly, e.g. that the pupil is shown clearly on display 34, they may push a start button, which may initiate an examination procedure. In some embodiments, once a user or a healthcare provider sees that the eye is positioned properly, e.g. that the pupil is shown clearly on display 34, an indication that the user should close or leave open the non-tested eye may be provided once the user or healthcare provider push a start button, which may initiate an examination procedure.

In some embodiments of the present invention, an examination protocol may include a stimulus protocol period during which the desired/configured stimulus protocol is executed, a preceding no-stimulation period before the beginning of the stimulus protocol execution, and/or a following no-stimulation period after the end of the stimulus protocol execution. Camera 11 may start capturing images and transmitting the images to processor 42 and/or processor 38 in the preceding no-stimulation period and/or proceed capturing images transmitting the images to processor 42 and/or processor 38 in the following no-stimulation period. For example, a preceding no-stimulation period may last 5 to 60 seconds before the beginning of the stimulus protocol execution. For example, a following no-stimulation period may last for a variable amount of time (for example 10 to 60 seconds) after the end of the stimulus protocol execution. Accordingly, during the entire examination protocol execution, processor 42 and/or processor 38 may detect the pupil contour and/or size in the stream of images and display the stream of images along with the corresponding overlay pupil contour and/or size value, for example in real time, as shown, for example, in FIG. 10A.

Figure 10B:
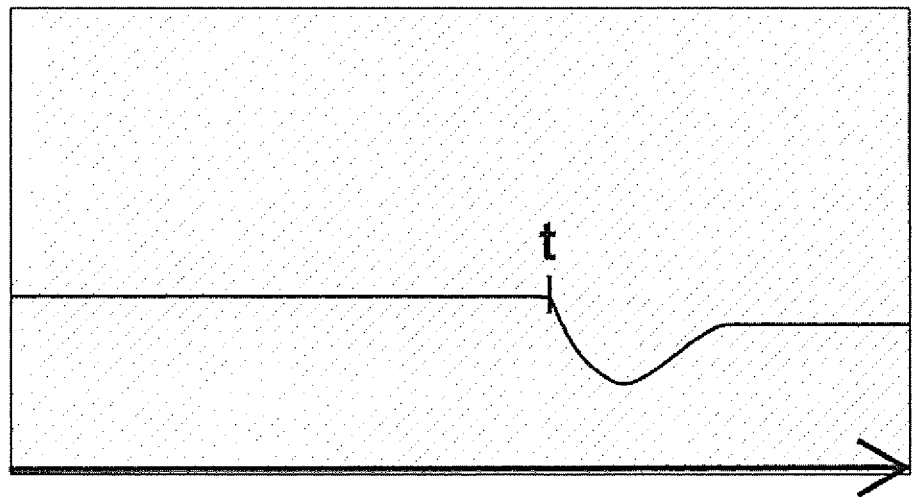
FIG. 10B is a schematic illustration of a pupil-metric response graph, according to some embodiments of the present disclosure.

In some embodiments, accuracy of pupil detection may be enhanced by adjusting, for example by the GUI, a threshold parameter or changing the region of interest used by processor 42 and/or processor 38 for the pupil detection. For example, the accuracy adjustment may be performed by a user during a preceding no-stimulation period and/or a following no-stimulation period, for example according to the displayed images and corresponding overlay pupil contours. Processor 42 and/or processor 38 may generate and present by the GUI a pupil-metric graph showing the pupil constriction change as a function of light exposure, e.g. the pupil diameter changes as a function of the intensity of the light stimulus, as shown, for example, in FIG. 10B. For example, the presented graph may facilitate a better refinement of the pupil contour detection threshold and region of interest selection by the user. For example, at time 1, a one-second stimulus may be provided to the eye, such as a one-second blue full field flash or any other suitable stimulus, resulting in a pupil constriction presented by the generated pupil-metric graph.

Processor 42 and/or processor 38 may obtain pupil-metric parameters and/or eye movement and/or generate the pupil-metric and/or eye movement graph based on a chronological set of pupil size values, each corresponding to another image in the image stream. Processor 42 and/or processor 38 may generate the set of values by removing artifacts from the image stream, such as images captured during blinks of the eye, blurred images, distorted images and/or other image types which cannot be used by processor 42 and/or processor 38 for pupil contour and/or size calculation. For example, processor 42 and/or processor 38 may execute a circularity quality control procedure on the vertical and horizontal diameter of the detected pupil, in order to detect artifact images.

Processor 42 and/or processor 38 may obtain eye movement parameters and/or generate an eye-movement graph based on a chronological set of eye movement values, each corresponding to another image in the image stream. Such graph may provide indication on the direction and distance the eye has moved during examination and/or as in response to visual stimuli or images shown on the screening or computing device and/or in correlation to the pupil-size values and/or pupil-metric parameters.

Processor 42 and/or processor 38 may analyze the set of pupil-size values to collect pupil-metric parameters such as, for example, the amplitude of pupil constriction (% from baseline), latency of pupil constriction (milliseconds), speed of pupil constriction (%/second), baseline pupil size (millimeters), pupil re-dilation speed (%/second), post-illumination pupil response (%) and/or area under a pupillary response curve.

Processor 42 and/or processor 38 may analyze other parameters such as the duration of the pupillary response, blink rates, fixation losses, as well as the amplitude, latency, gain, velocity and peak velocity of ocular movement, and the percent time spent in a region of interest in the presented stimulation, eye movement, eye movement amplitude, eye movement velocity, eye movement peak velocity, eye movement percent time spent in a region of interest, parameters computed via machine learning from pupillographic, and ocular movement traces. The Processor 42 and/or processor 38 may generate various alerts based on the analyzed changes of the above numerated parameters.

Figure 11:
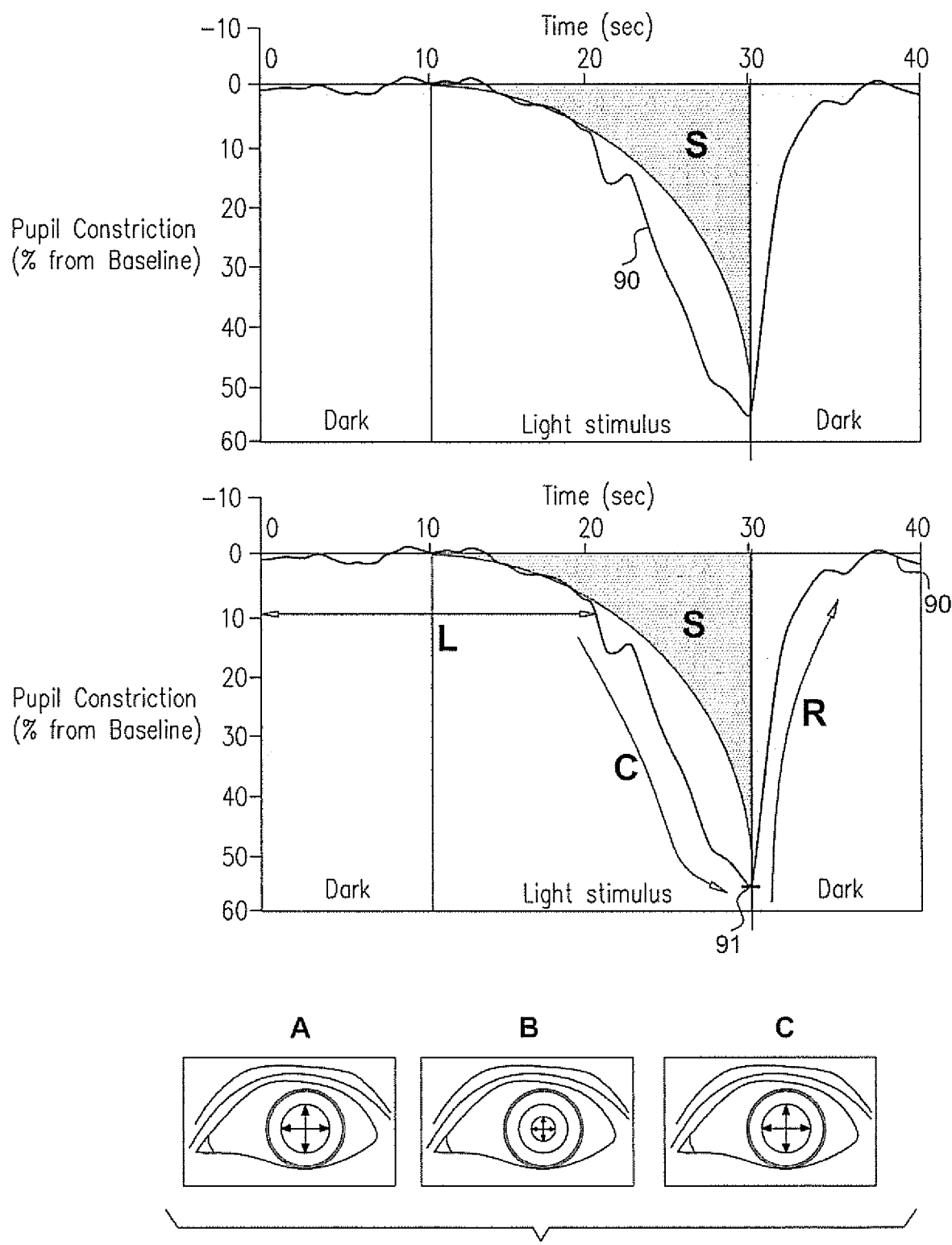
FIG. 11 is a schematic illustration of exemplary analysis made by processor 42 and/or processor 38 to obtain some pupil-metric response parameters, according to some embodiments of the present disclosure.

Reference is now made to FIG. 11, which is a schematic illustration of exemplary analysis made by processor 42 and/or processor 38 to obtain pupil-metric parameters, according to some embodiments of the present invention. For example, screening device 10 may perform a pre-defined and/or user defined ramp-up examination protocol. For example, the examination protocol may include 10 seconds of a preceding no-stimulation period, 20 seconds of logarithmic ramp-up stimulus protocol represented by the gray area S, and 10 seconds of a following no-stimulation period. For example, the stimulus protocol may include a ramp up of the illumination from 8 to 14.5 Log photons. Graph 90 shows the set of pupil size values obtained during execution of the examination protocol. A baseline pupil size A may be used to normalize the pupil diameter measurements, i.e. to calculate the changes in the pupil size in % from the baseline size A, as shown in graph 90. Baseline pupil size A may be the pupil size at the beginning of the examination and/or during the preceding no-stimulation period. At the end of the 20 seconds ramp-up stimulus protocol, the pupil may be at maximal constriction with pupil size B, during the following no-stimulation period, the pupil may re-dilate to a size C. Accordingly, from the set of pupil size values, processor 42 may obtain pupil-metric parameters such as constriction amplitude 91 (in % from the baseline), latency L (in seconds), constriction speed C (in %/second) and pupil re-dilation speed R (%/seconds).

Processor 42 and/or processor 38 may analyze at least some of these parameters to evaluate the risk of ocular or neurological disease. For example, processor 42 and/or processor 38 may calculate, based on at least some of these parameters, a Pupil-graphic Index (Pix) value for the examined eye, representing ocular and neurological integrity of the examined eye, e.g. a probability that the user has ocular and/or neurological malfunctioning. The Pix may be computed, for example, by execution of a classification engine and/or based on comparison of the obtained parameters to reference data stored in a database 60, for example a secure cloud database.

Processor 42 and/or processor 38 may generate a plotted pupil-graphic trace, e.g. a graph showing the changes in the pupil size during execution of the examination protocol. Processor 42 and/or processor 38 may generate a plotted eye-graphic trace, e.g. a graph showing the movement of the eye during execution of the examination protocol.

Figure 12:
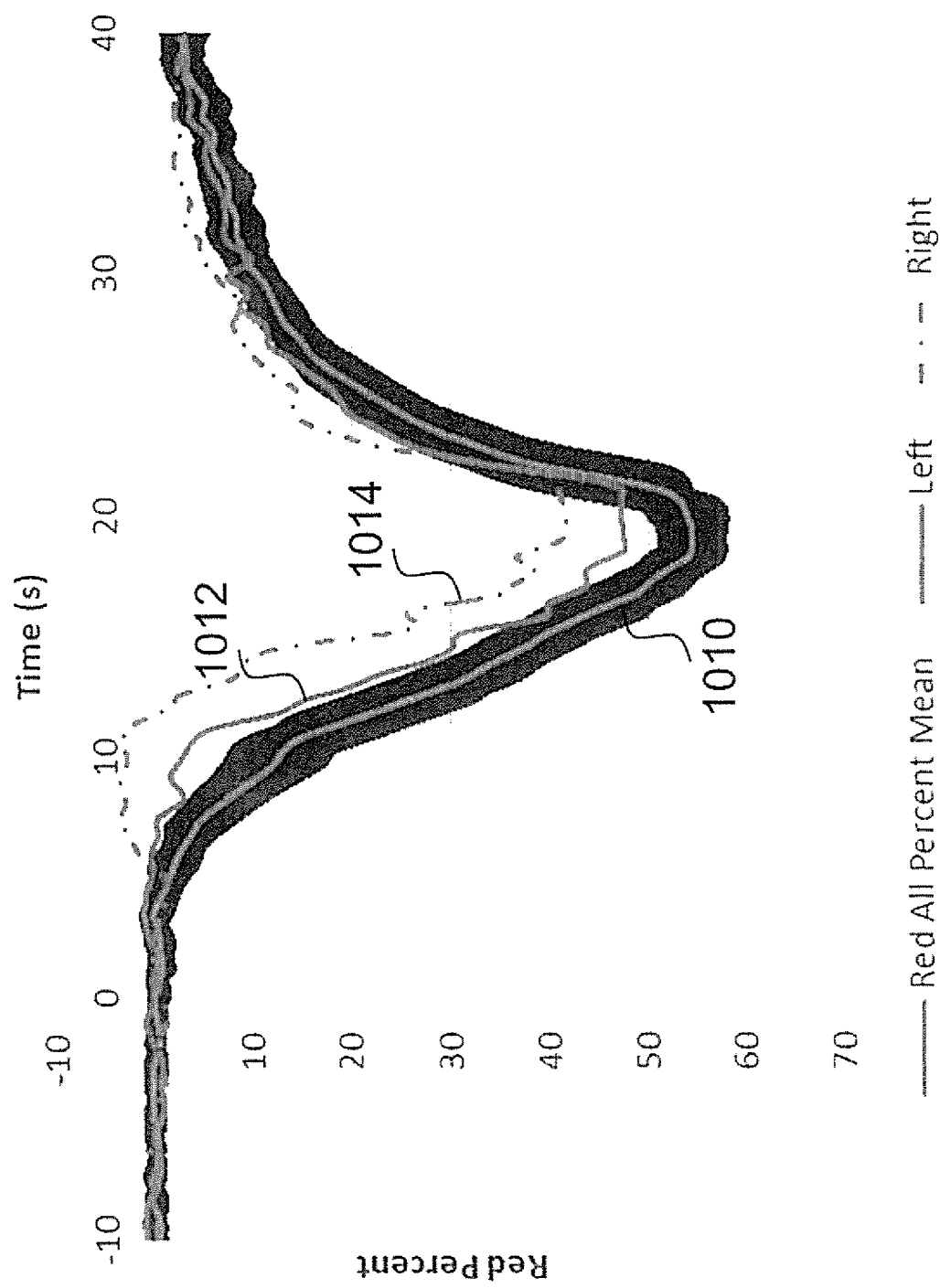
FIG. 12 is a schematic illustration of plotted pupil-graphic light response traces, according to some embodiments of the present disclosure.
Figure 12:
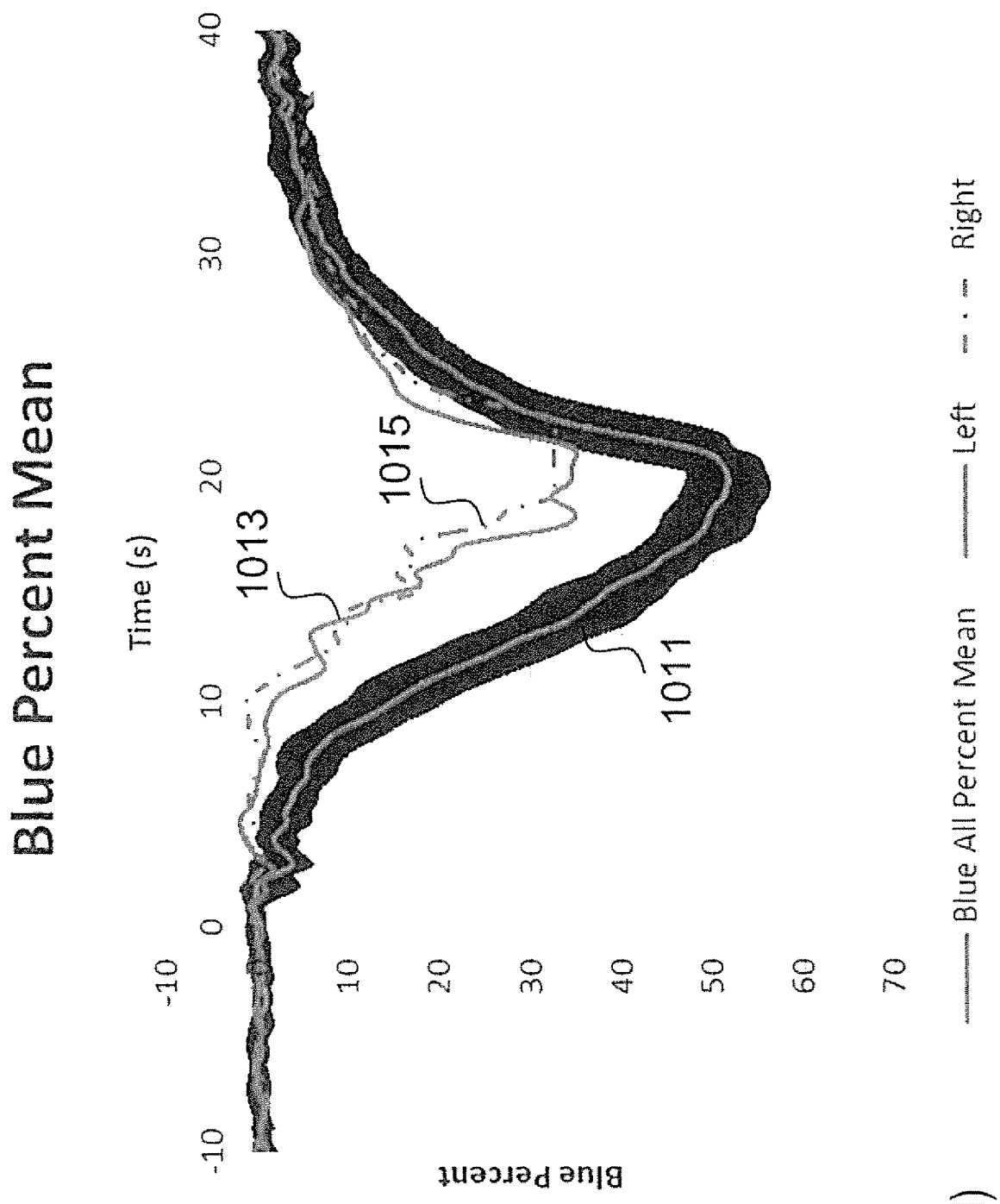

Reference is now made to FIG. 12, which is a schematic illustration of plotted pupil-graphic traces, according to some embodiments of the present invention. FIG. 12 shows an exemplary pupil-graphic trace in a patient compared to a group of healthy patients making up a control group of ±95% CI. FIG. 12 shows a pupil-graphic trace for red light stimulation and a pupil-graphic trace for a blue light stimulation. The dark regions represent normal pupil-metric data stored in database 60, i.e. of users with low risk of ocular and/or neurological malfunctioning. The lines inside the dark regions represent the mean of the normal pupil-metric data. The lines outside the dark regions represent abnormal pupil-graphic traces that may imply high risk of ocular and/or neurological malfunctioning. Processor 42 and/or processor 38 may output results of the analysis, including the plotted pupil-graphic trace(s) and/or optional implications. For example, in case high risk of ocular and/or neurological malfunctioning is implied by the results, processor 42 and/or processor 38 may provide an indication to the user, for example an alert urging the user to consult with a professional.

Figure 13A:
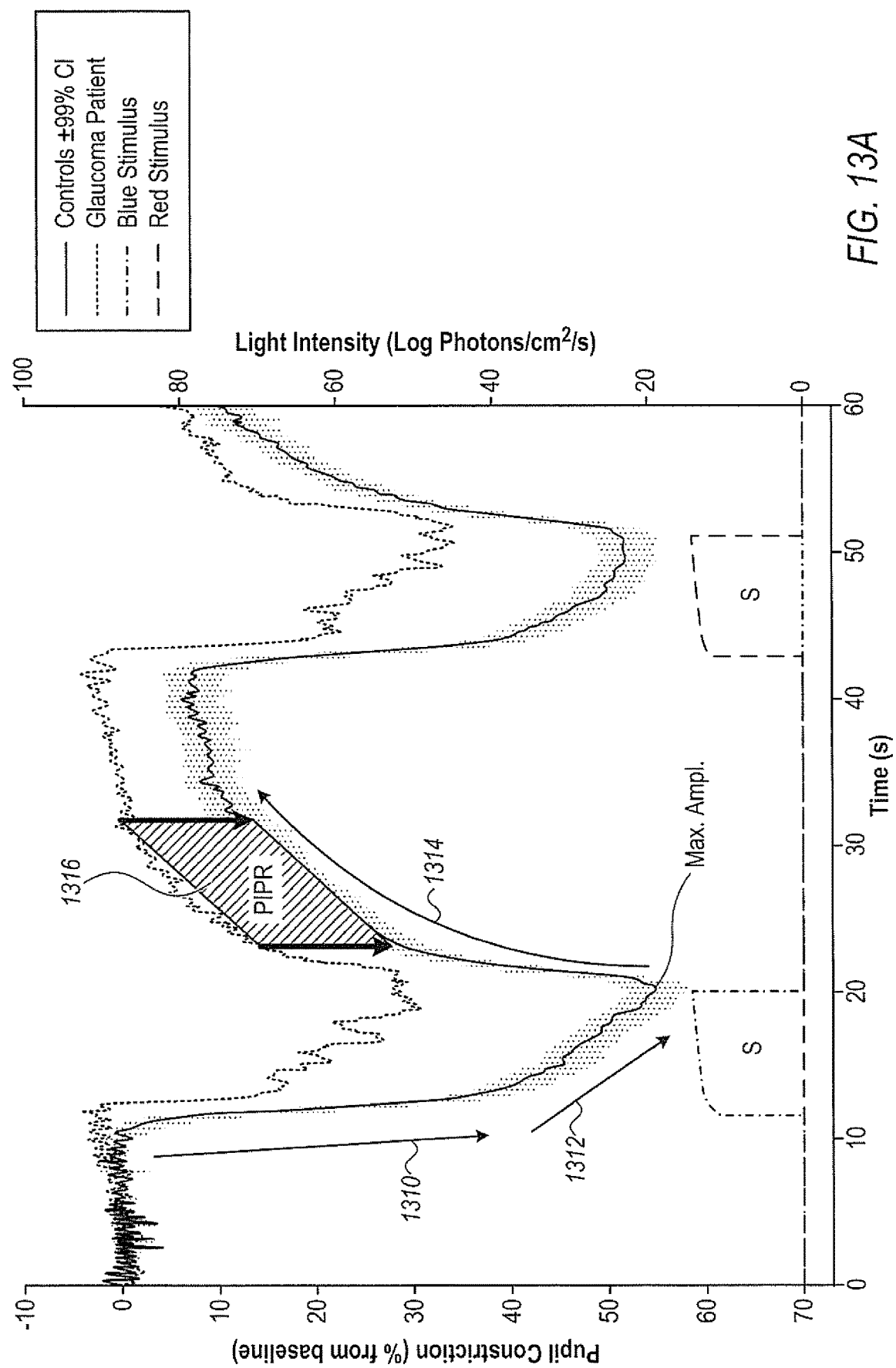
FIGS. 13A-C, are schematic illustrations of pupillometric trace in glaucoma patient compared to a group of healthy controls, in patient with moderate diabetic retinopathy compared to a group of healthy controls, and in a patient with thyroid eye disease before and after steroid treatment, respectively, according to some embodiments of the present disclosure.
Figure 13B:
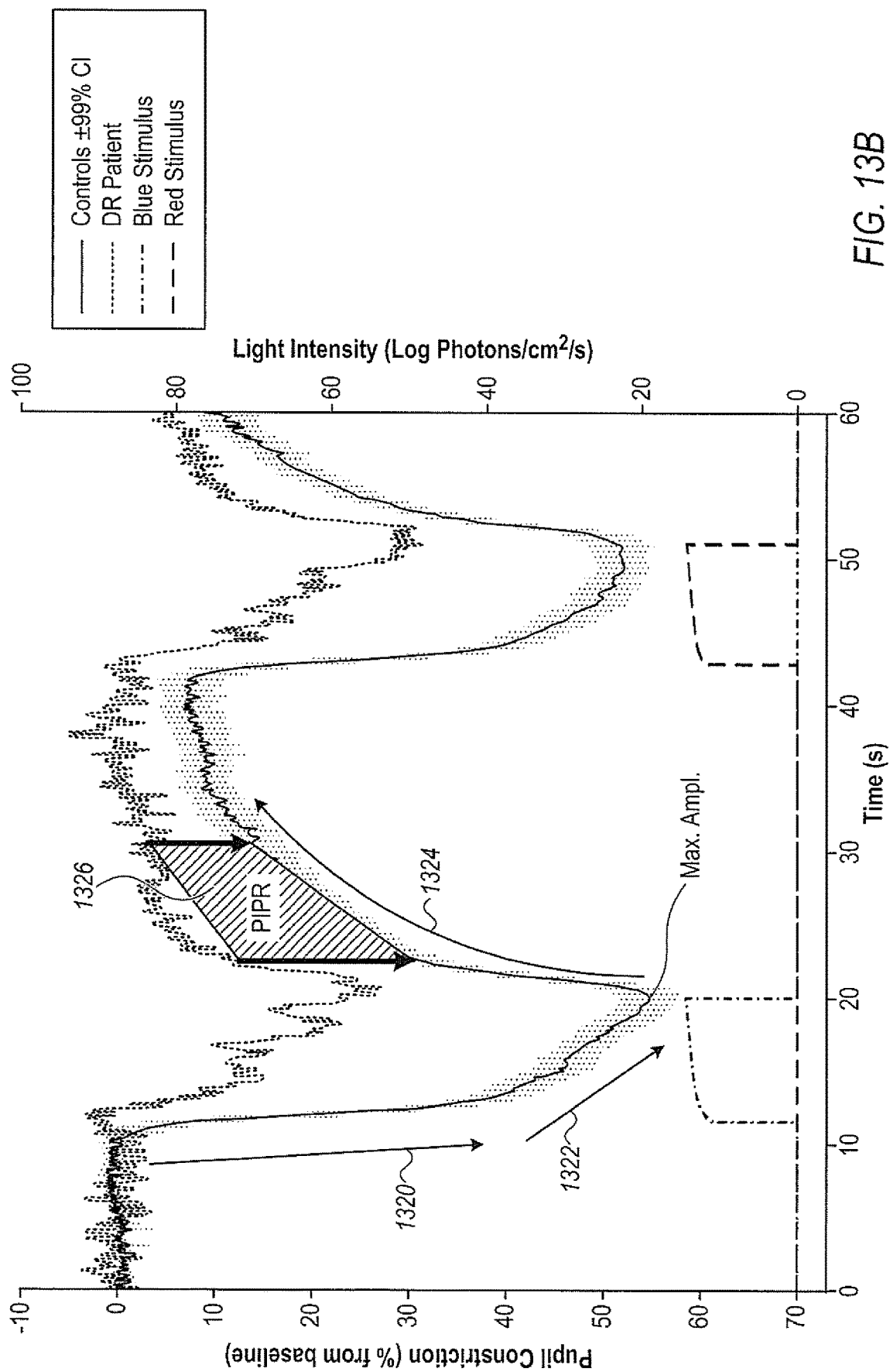
Figure 13C:
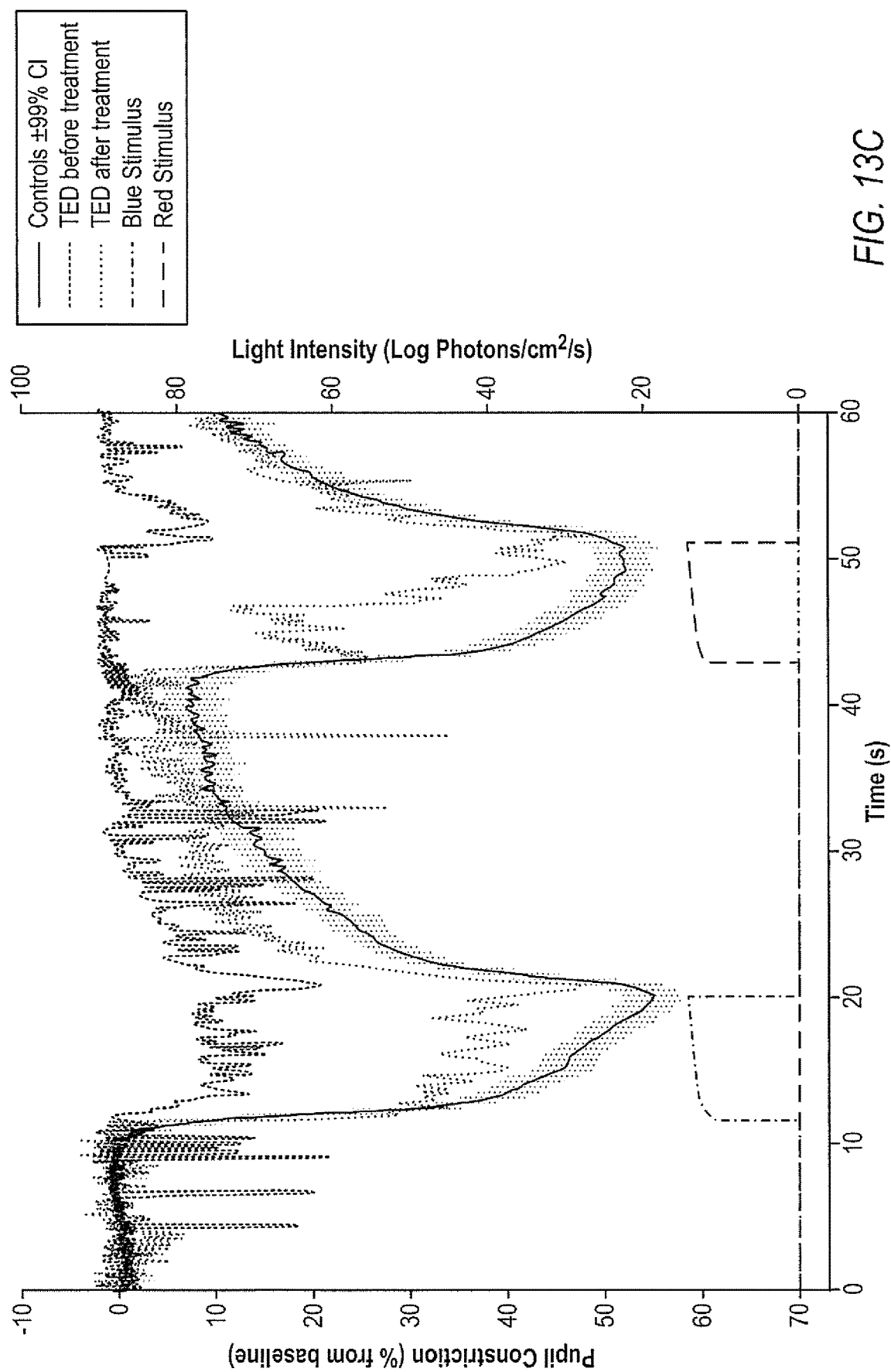

Reference is now made to FIGS. 13A-C, which are schematic illustrations of pupillometric trace in glaucoma patient compared to a group of healthy controls, in patient with moderate diabetic retinopathy compared to a group of healthy controls, and in a patient with thyroid eye disease before and after steroid treatment, respectively, in accordance with some embodiments of the present invention. According to FIG. 13A, an example of pupillometric trace in a glaucoma patient compared to a group of healthy controls, is provided. The number of healthy controls was 59 people (n=59; ±99% Confidence interval). The phasic responses, e.g., phasic constriction 1310, and redilation 1314, to blue and red light paradigms (illustrated at the bottom of FIG. 13A) are reduced in the glaucoma patient compared to healthy controls. In addition, the maximal amplitude of gradual constriction 1312 is lower in the glaucoma patient compared to the control group. The gradual constriction slope 1312 and Post Illumination Pupillary response (PIPR) 1316 in the glaucoma patient are attenuated compared to healthy controls. Once all or most of the features, i.e., phasic constriction, gradual constriction, redilation, and PIPR of a user are similar to those illustrated in FIG. 13A, specifically that the above-mentioned features are lower compared to those of a healthy control group, a user with possibly undiagnosed glaucoma may be prompted by the dedicated software application that is installed on user computing device 30, to seek medical attention from a healthcare provider, e.g., a glaucoma specialist. That is, the screening device and system of the present disclosure may be used to monitor the progression of ocular diseases, and indicate whether further professional advice is required.

According to FIG. 13B, an example of pupillometric trace in a patient with moderate diabetic retinopathy (DR) compared to a group of healthy controls, is provided. The number of healthy controls was 59 people (n=59; ±99% Confidence interval). The phasic constriction response to blue and red stimulus, e.g., phasic constriction 1320 is reduced in the DR patient compared to the control group. In addition, the maximal amplitude of the gradual constriction 1322 is lower in the DR patient compared to the maximum of the control group. The phasic constriction slope 1322 and PIPR 1326 are attenuated compared to healthy controls. Once all or most of the features, i.e., phasic constriction, gradual constriction, redilation, and PIPR of a user are similar to those illustrated in FIG. 13B, specifically that the above-mentioned features are lower compared to those of a healthy control group, a user with possibly undiagnosed DR may be prompted by the dedicated software application that is installed on user computing device 30, to seek medical attention from a healthcare provider, e.g., a glaucoma specialist. That is, the screening device and system of the present disclosure may be used to monitor the progression of ocular diseases, and indicate whether further professional advice is required.

Figure 14:
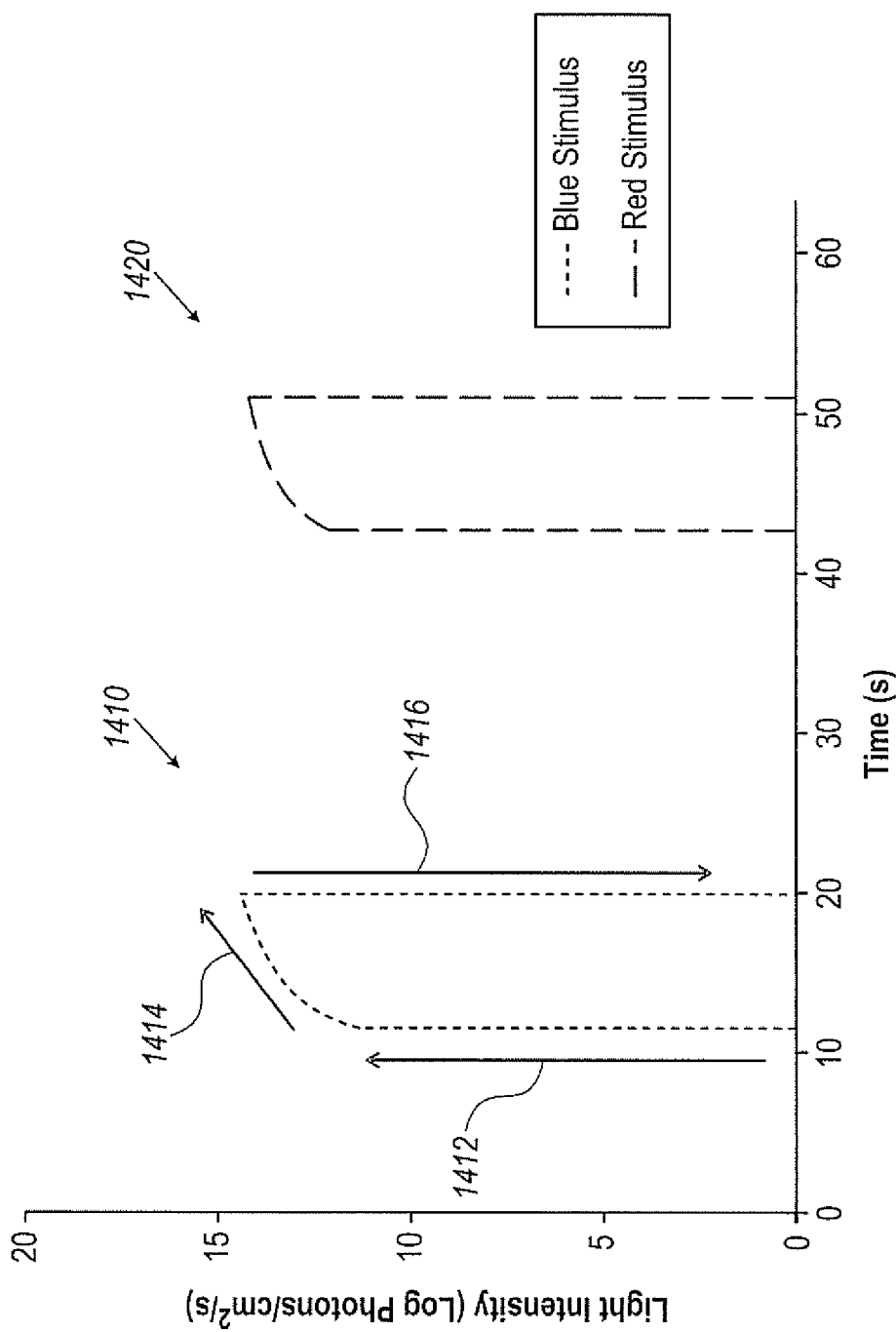
FIG. 14 is a schematic illustration of a light delivery protocol, according to some embodiments of the present disclosure.

According to FIG. 13C, an example of pupillometric trace in a patient with thyroid eye disease (which may cause vision loss by compression of the optic nerve) before and after treatment with steroids, is provided. The pupillary light responses to blue and red stimulus were obliterated by the compression of the optic nerve compared to a group of healthy controls (n=59; ±99% Confidence interval). After treatment with steroids the patient recovered with respect to visual acuity and the pupillary light response improved to both blue and red light stimulus. The improvement in the pupillary light response, e.g., that the difference between the patients' light responses compared to those of the control group was smaller after steroid treatment, is an indicator of the success of the steroid treatment. That is, the screening device and system of the present disclosure may be used to assess ocular integrity and to monitor efficacy of treatments in ocular and neurodegenerative diseases. Reference is now made to FIG. 14, which is a schematic illustration of a light delivery protocol, according to some embodiments of the present invention. FIG. 14 illustrates a light delivery protocol for the detection of ocular diseases such as glaucoma and diabetic retinopathy. The light delivery protocol includes a first (e.g., blue) stimulus 1410 and a second (e.g., red) stimulus 1420. The protocol illustrated in FIG. 14 occurs is of 30 to 60 seconds in duration. The protocol begins with a dark period of between 5 to 15 seconds, during which a user's eye adapts to lack of light. Following the dark period, a fast onset of light 1412 of a first chromaticity (e.g., blue stimulus 1410) may include an abrupt and very quick increase of light intensity from zero to mesopic light levels sufficient to stimulate retinal cones and rods. A gradual increase of light intensity 1414 to high photopic levels, which stimulate the photoreceptors in the inner retina (intrinsically photosensitive retinal ganglion cells (ipRGCs)) may follow the abrupt light intensity increase 1412. The duration of light exposure to the user's eye may range from one to ten seconds. Ten to 20 seconds following light offset 1416, another light stimulation of different chromaticity (e.g., red stimulus 1420) may be initiated following a similar temporal pattern to that of the first chromaticity.

A version of the predefined light delivery protocol detailed hereinabove was evaluated in over 500 participants with and without ocular diseases. The protocol consisted of an initial dark adaptation period of 10 seconds, followed by an acute onset of blue light (12 Log/Photons/cm2/sec) then a gradual exponential increase to 14.5 Log photons for 10 seconds. Twenty seconds following blue light offset, an acute onset of red light (12 Log/Photons/cm2/sec) was initiated, followed by a gradual exponential increase to 14.5 Log photons for 10 seconds and a dark exposure (i.e., no light exposure) for 10 seconds. The acute onset of light 1412 may assist in evaluating the fast phasic pupillary response (for example, phasic constriction 1310, FIG. 13A) and the gradual increase in light may assist in evaluating the sustained gradual pupil constriction (for example, gradual constriction 1312, FIG. 13A). In addition, the light paradigm of FIG. 14 may cause a persistent pupillary constriction after blue light offset 1416 or a post-illumination pupillary response (PIPR) that is a proxy for the assessment of ipRGCs and inner retina integrity. This new paradigm or protocol enables the assessment of additional pupillometric features such as the phasic response (e.g., phasic constriction 1310, FIG. 13A) and the PIPR (e.g., PIPR 1316 of FIG. 13A), which are not detectable while using the light protocol described with respect to FIG. 11. In addition, this new light paradigm of FIG. 14 yielded high accuracy in detecting pupillometric dysfunction and ocular diseases such as glaucoma (see FIG. 13A) or diabetic retinopathy (see FIG. 13B).

Figure 15B:
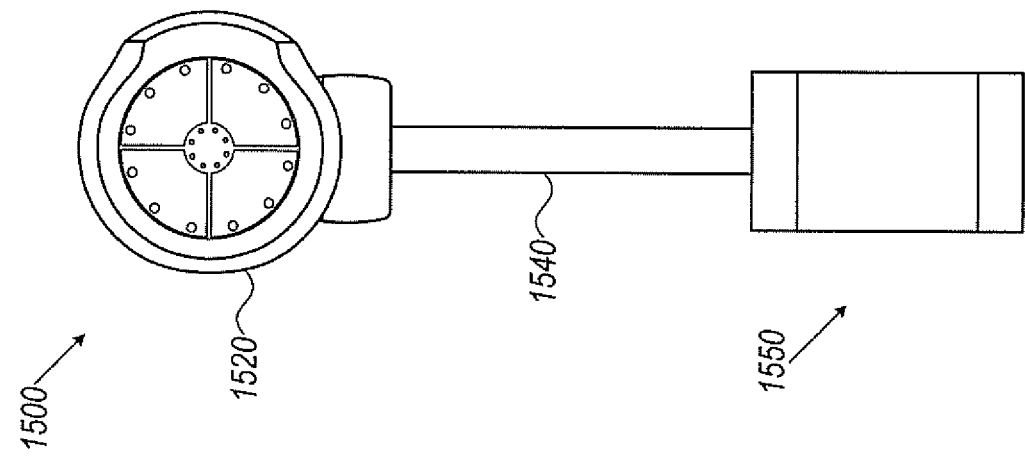
FIGS. 15A-15B are schematic illustrations of perspective view and front view of a device including a clip-on fixture for ocular and/or neurological screening, according to some embodiments of the present disclosure.
Figure 15A:
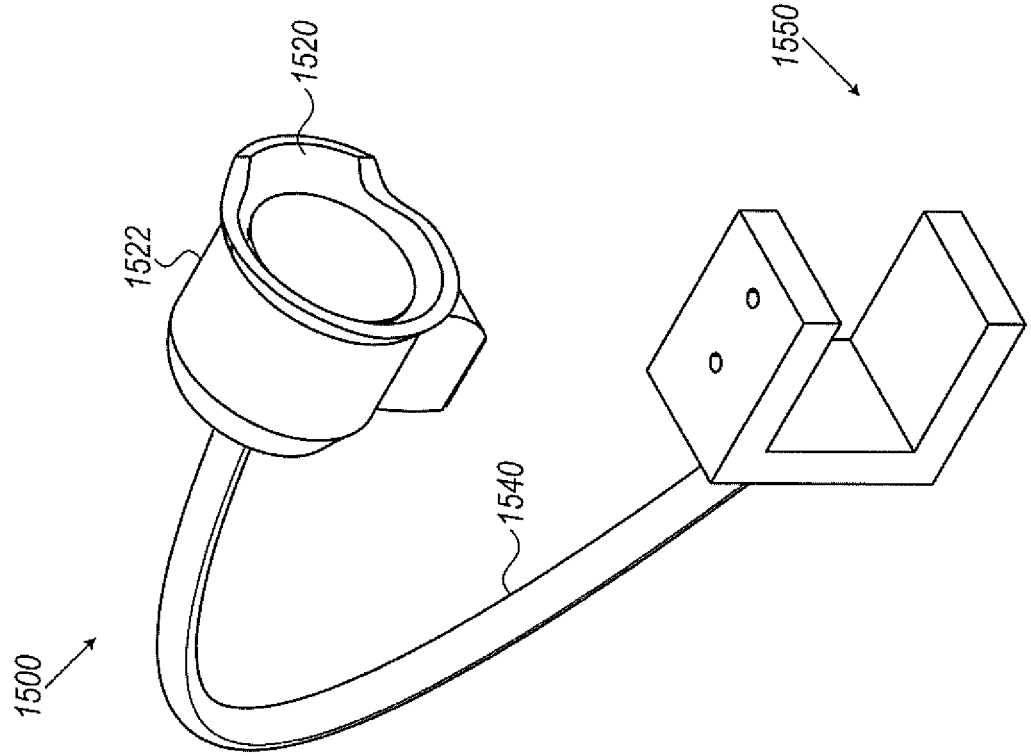

Reference is now made to FIGS. 15A-15B, which are schematic illustrations of perspective view and front view of a hand-held sized device including a clip-on fixture for ocular and/or neurological screening, according to some embodiments of the present invention. According to some embodiments, instead of a hand-held device, e.g., hand-held screening device 10, the hand-held sized screening device, e.g., device 1500 may include a clip-on fixture to enable a fixed attachment of device 1500 to a desktop of a user or of a healthcare or to any portable ophthalmic apparatus. For example, device 1500 may be attached to a table or desk, or to any of the following portable ophthalmic apparatuses: refractometers, optical coherence tomography devices, fundus cameras, slit lamp examination equipment, trial Frame Refraction, or any other device that may be present at an eye care or healthcare practitioner's office. Screening device 1500 may comprise housing 1522, and eyepiece 1520, which may be similar to those of hand-held screening device 10. Device 1500 may further include a clip-on fixture 1550, which may be connected to housing 1522 via a semi-rigid cable 1540. In some embodiments, clip-on fixture 1550 may have two arms 1550A, and 1550B, which are configured to hold or be attached to a desk or table such that the desk or table may be held between first arm 1550A and second arm 1550B. For example, first arm 1550A may be positioned on top of the edge of a desk or table, while the second arm 1550B may be located beneath the edge of the desk or table. In other embodiments, clip-on fixture 1550 may include other fixating configurations. In some embodiments, cable 1540 may enable movement and adjustment of housing 1522 such to conform to the position of a user in order to enable a proper and convenient screening process.

Figure 15D:
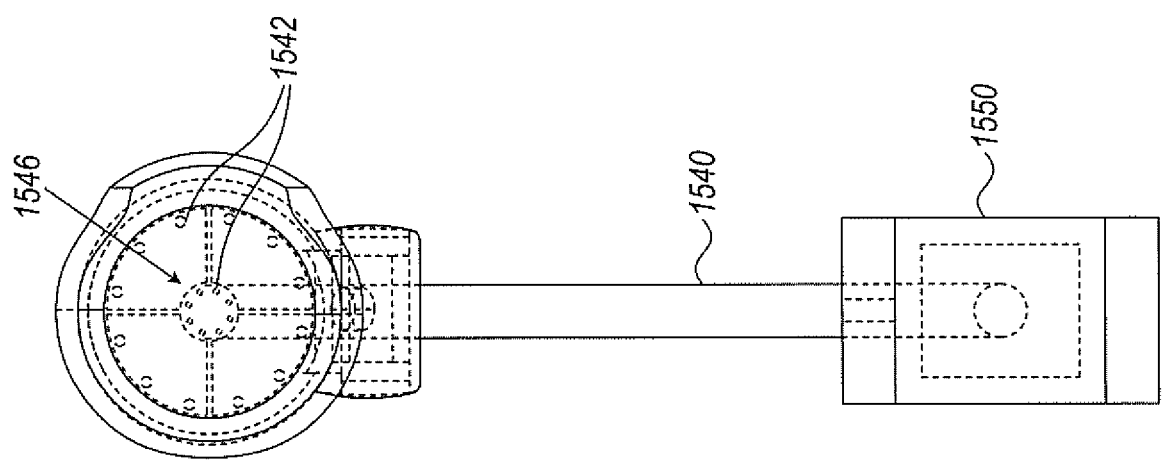
FIGS. 15C-15D are schematic illustrations of perspective view and front view of a device including a clip-on fixture for ocular and/or neurological screening, including inner components, according to some embodiments of the present disclosure.
Figure 15C:
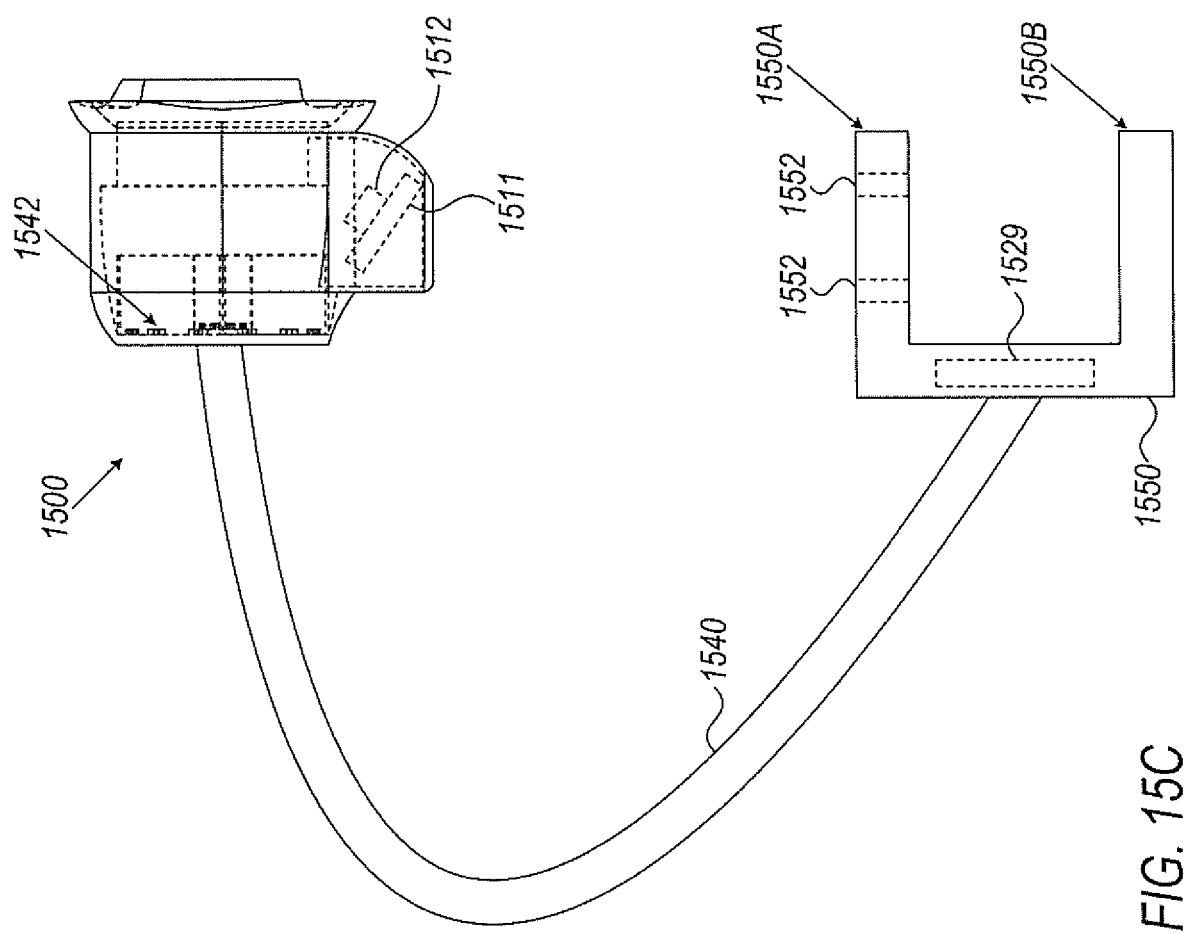

Reference is now made to FIGS. 15C-15D, which are schematic illustrations of perspective view and front view of a hand-held sized device including a clip-on fixture for ocular and/or neurological screening, including inner components, according to some embodiments of the present invention. In some embodiments, housing 1522 may encapsulate camera 1511, which may include an IR filter, as well as an IR illumination source 1512. Camera 1511 and IR illumination source 1512 may be inclined towards the opening of eyepiece 1520. Camera 11 may be configured to capture images of the user's eye. Housing 1522 may further encapsulate RGB or other illumination sources, e.g., RGB LEDs 1542, which may be configured to stimulate the user's eye during the screening or examination process. According to some embodiments, RGB illumination sources 142 and 146 may be positioned in segmented orientations, as detailed with respect to FIG. 6.

In some embodiments, PCB 1529 may be located within clip-on fixture 1550, though in other embodiments, PCB 1529 may be located within housing 1522. In some embodiments, electronics 1529 may include a charging port for charging the power source of device 1500.

According to some embodiments, arm 1550A may include holes through which screws, bolts, rivets or other fastening means may be inserted in order to fasten clip-on fixture 1550 to the desk, table or any portable apparatus. It should be noted that any screening process and any results, such as pupillometric trace, mentioned along the disclosure, may be performed by either the hand-held screening device, e.g., device 10, or by a clip-on hand-held sized screening device, e.g., device 1500.

According to some embodiments, the screening of ocular and neurological diseases may be easily performed following a button press, either on the screening device, e.g., screening device 10, or on the user computing device, e.g., device 30. The screening process may monitor, determine and initiate several eye related and data analysis features, among which are: pupil localization, pupil contour detection, launch of light paradigm, data collection, and data transmission via a dedicated software application to a secure cloud database, e.g., database 60 (FIG. 1). In some embodiments, analysis of videos or pupillometric traces (as illustrated, for example, in FIGS. 13A-13C) may be performed instantaneously by the software or through a cloud service, and pupillometric features, for example, any one or a combination of: amplitude of pupil constriction, latency of pupil constriction, speed of pupil constriction, baseline pupil size, pupil re-dilation speed, post-illumination pupil response, area under a pupillary response curve, the duration of the pupillary response, blink rates, fixation losses, ocular movement amplitude, ocular movement latency, ocular movement gain, ocular movement velocity, peak velocity of ocular movement, the percent time spent in a region of interest in the presented stimulation, eye movement, eye movement amplitude, eye movement velocity, eye movement peak velocity, eye movement percent time spent in a region of interest, parameters computed via machine learning from pupillographic, and ocular movement traces, may compared to a database of healthy controls or of other patients with ocular conditions.

The database of healthy controls and of other patients suffering from similar diseases may be stored in the software of in the secure cloud database. The outcome of a comparison between a current screened user and healthy controls (or other patients) may lead the user to seek medical attention. The screening device or the user's computing device, which communicates with the screening device, may prompt a text message and/or a color indication whereby different colors indicate a different risk level, in case an abnormal pupillary response is detected (for example, by analyzing the plots of FIGS. 13A-13C, and FIG. 14). For example, an indicator of risk of ocular disease may include, for example, a text message that may read as follows: "Please see your eye doctor". A color indication may include one of a list of colors, each indicating a different risk level, for example: a red color may indicate high risk, bright orange may indicate moderate risk, and light blue may indicate low risk. In case the response of the user's eye to the screening process is similar to the response of healthy controls, the software installed on the user's computing device, e.g., device 30, or on the screening device, may cause prompt of a text or color indication that no risk is present. For example, a text indication may include: "No eye disease suspected". The software may also provide a list of health specialists near the location of the user, which may be presented on the user's computing device, e.g., device 30.

In the context of some embodiments of the present disclosure, by way of example and without limiting, terms such as 'operating' or 'executing' imply also capabilities, such as 'operable' or 'executable', respectively.

Conjugated terms such as, by way of example, 'a thing property' implies a property of the thing, unless otherwise clearly evident from the context thereof.

The terms 'processor' or 'computer', or system thereof, are used herein as ordinary context of the art, such as a general purpose processor, or a portable device such as a smart phone or a tablet computer, or a micro-processor, or a RISC processor, or a DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory.

The terms 'software', 'program', 'software procedure' or 'procedure' or 'software code' or 'code' or 'application' may be used interchangeably according to the context thereof, and denote one or more instructions or directives or electronic circuitry for performing a sequence of operations that generally represent an algorithm and/or other process or method. The program is stored in or on a medium such as RAM, ROM, or disk, or embedded in a circuitry accessible and executable by an apparatus such as a processor or other circuitry. The processor and program may constitute the same apparatus, at least partially, such as an array of electronic gates, such as FPGA or ASIC, designed to perform a programmed sequence of operations, optionally comprising or linked with a processor or other circuitry.

The term 'configuring' and/or 'adapting' for an objective, or a variation thereof, implies using at least a software and/or electronic circuit and/or auxiliary apparatus designed and/or implemented and/or operable or operative to achieve the objective.

A device storing and/or comprising a program and/or data constitutes an article of manufacture. Unless otherwise specified, the program and/or data are stored in or on a non-transitory medium.

In case electrical or electronic equipment is disclosed it is assumed that an appropriate power supply is used for the operation thereof.

The flowchart and block diagrams illustrate architecture, functionality or an operation of possible implementations of systems, methods and computer program products according to various embodiments of the present disclosed subject matter. In this regard, each block in the flowchart or block diagrams may represent a module, segment, or portion of program code, which comprises one or more executable instructions for implementing the specified logical function(s). It should also be noted that, in some alternative implementations, illustrated or described operations may occur in a different order or in combination or as concurrent operations instead of sequential operations to achieve the same or equivalent effect.

The corresponding structures, materials, acts, and equivalents of all means or step plus function elements in the claims below are intended to include any structure, material, or act for performing the function in combination with other claimed elements as specifically claimed. As used herein, the singular forms "a", "an" and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or groups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

The invention claimed is:

1. A hand-held sized ocular and neurological screening device comprising:
    eyepiece; and
    a hand-held housing comprising:
        a tubular stimulus chamber defining a light stimulus channel, wherein an illumination source is configured to provide light stimulus towards an opening through the light stimulus channel, said stimulus chamber comprising barriers for dividing the stimulus channel to sub channels; and
        an operational chamber comprising:
            an infrared camera positioned outside the stimulus channel and inclined towards the opening, the infrared camera is configured to capture images through the opening without interfering with the light stimulus; and
            a controller configured to:
                receive the captured images from the infrared (IR) camera; and
        control an illumination panel at a distal end of the stimulus channel and the infrared (IR) camera parameters to provide illumination separately to each of the sub channels.

2. The device of claim 1, wherein the light stimulus channel further comprises an opening at a proximal end, the opening at the proximal end is configured to engage with the eyepiece.

3. The device of claim 1, wherein the controller is further configured to transmit the captured images, videos or any other digital signal to an external computing device or directly to a cloud storage system associated with the screening device.

4. The device of claim 3, wherein the external computing device is a user computing device.

5. The device of claim 3, wherein the external computing device is an external server.

6. The device of claim 1, wherein the controller is further configured to receive instructions from an external computing device and to control the illumination panel and the infrared camera parameters according to the received instructions.

7. The device of claim 1, wherein the stimulus chamber comprises at least one optical apparatus between the illumination panel and the opening.

8. The device of claim 1, wherein a diffuser is located less than a distance that allows accommodation of a human eye, from a rim of the eyepiece to an eye of a user of the device.

9. The device of claim 1, wherein the operational chamber comprises at least one infrared light source outside the stimulus channel providing infrared illumination towards the opening.

10. The device of claim 1, wherein the barriers divide the stimulus channel to quadrant sub channels and a central sub channel.

11. The device of claim 1, wherein the eyepiece comprises an eye support having an extended lip and a connector for engagement with the opening of the housing, the connector having two opposite gaps, wherein the gaps enable the camera to capture images via the opening when the extended lip is oriented in a temporal direction.

12. The device of claim 1, wherein the infrared camera is positioned outside the stimulus channel at an inclination of about 60 degrees towards the opening through the light stimulus channel.

13. The device of claim 1, wherein said device further comprises a clip-on fixture for fixing the device onto an apparatus selected from a group consisting of a table, a desktop, and a portable ophthalmic apparatus.

14. The device of claim 13, wherein said portable ophthalmic apparatus comprises an apparatus selected from a group consisting of refractometers, optical cohereace tomography devices, fundus cameras, slit lamp examination equipment, trial Frame Refraction, and any other device that may be present at an eye care or healthcare practitioner's office.

15. The device of claim 13, wherein said device comprises a first arm and a second arm such that said apparatus is held between the first arm and the second arm of the device.

16. A system for ocular and neurological screening comprising:
    an application server configured to communicate with a user device via a software application installed in the user device; and
    a hand-held sized pupil screening device comprising:
        an eyepiece; and
        a hand-held housing comprising:
            a tubular stimulus chamber defining a light stimulus channel, comprising illumination panel at a distal end and an opening at a proximal end, the opening is configured to engage with the eyepiece wherein the illumination panel is configured to provide light stimulus towards an opening through the light stimulus channel, said stimulus chamber comprising barriers for dividing the stimulus channel to sub channels; and
            an operational chamber comprising an infrared camera configured to capture images through the opening without interfering with the light stimulus and to transmit the captured images, and a controller configured to receive instructions from the application server and to control the illumination panel according to the received instructions and the infrared (IR) camera parameters to provide illumination separately to each of the sub channels,
    wherein the application server is configured to analyze changes in a pupil in the received images and calculate based on the changes in the pupil size or position a value indicative of an ocular or neurological disorder.

17. The system of claim 16, wherein the application server is configured to transmit an alert to the user device in case calculated value implies abnormal ocular or neurological functioning.

18. The system of claim 16, wherein the application server is configured to receive from the user device an examination protocol and to provide instructions to the controller based on the received protocol.

19. The system of claim 16, wherein said hand-held pupil screening device further comprises a clip-on fixture for fixing the device onto an apparatus selected from a group consisting of: a table, a desktop, and a portable ophthalmic apparatus.

20. The system of claim 19, wherein said portable ophthalmic apparatus comprises an apparatus selected from a group consisting of refractometers, optical coherence tomogrtiphy devices, fundus cameras, slit lamp examination equipment, trial Frame Refraction, and any other device that may be present at an eye care or healthcare practitioner's office.

21. The system of claim 19, wherein said pupil screening device comprises a first arm and a second arm such that said apparatus is held between the first arm and the second arm of the device.

22. A method for ocular and neurological screening comprising:
   (i) providing to a controller, instructions to control an illumination panel in a hand-held sized ocular and neurological screening device, the device comprising:
      an eyepiece; and
      a hand-held housing comprising:
         a tubular stimulus chamber defining a light stimulus channel, wherein the illumination source is configured to provide light stimulus towards the opening through the light stimulus channel, said stimulus chamber comprising barriers for dividing the stimulus channel to sub channels; and
         an operational chamber comprising an infrared camera configured to capture images through the opening without interfering with the light stimulus and to transmit the captured images to an external computing device;
      and a controller configured to receive instructions from the external computing device and to control the illumination panel at a distal end of the stimulus channel according to the received instructions and the infrared (IR) camera parameters to provide illumination separately to each of the sub channels:
   (ii) receiving a stream of images from the camera; and
   (iii) analyzing changes in a pupil in the received images and calculating based on the changes a value indicative of ocular or neurological functioning.

23. The method of claim 22, further comprising the step presenting to a person being screened a visual stimulus.

24. The method of claim 22, wherein the changes analyzed are based on the changes in pupil size or eye movement.

25. The method of claim 23, wherein the changes analyzed are made in response to the visual stimulus presented to the person being screened.

26. The method of claim 22, wherein the changes analyzed are in the rate of change of the pupil size over the duration of the illumination.

27. The method of claim 22, wherein the change analyzed includes at least one of a list consisting of: the amplitude of pupil constriction, latency of pupil constriction, speed of pupil constriction, baseline pupil size, pupil re-dilation speed, post-illumination pupil response, area under a pupillary response curve, the duration of the pupillary response, blink rates, fixation losses, ocular movement amplitude, ocular movement latency, ocular movement gain, ocular movement velocity, peak velocity of ocular movement, the percent time spent in a region of interest in the presented stimulation, eye movement, eye movement amplitude, eye movement velocity, eye movement peak velocity, eye movement percent time spent in a region of interest, parameters computed via machine learning from pupillographic, and ocular movement traces.

\* \* \* \* \*